US009271678B2

United States Patent
Liao et al.

(10) Patent No.: US 9,271,678 B2
(45) Date of Patent: Mar. 1, 2016

(54) CONSTRAINED REGISTRATION FOR MOTION COMPENSATION IN ATRIAL FIBRILLATION ABLATION PROCEDURES

(75) Inventors: Rui Liao, Princeton Junction, NJ (US); Alexander Benjamin Brost, Erlangen (DE); Norbert Strobel, Heroldsbach (DE); Andreas Wimmer, Erlangen (DE); Joachim Hornegger, Effeltrich (DE)

(73) Assignees: SIEMENS AKTIENGESELLSCHAFT, Munich (DE); SIEMENS CORPORATION, Iselin, NJ (US)

( * ) Notice: Subject to any disclaimer, the term of this patent is extended or adjusted under 35 U.S.C. 154(b) by 941 days.

(21) Appl. No.: 13/410,444

(22) Filed: Mar. 2, 2012

(65) Prior Publication Data

US 2012/0271162 A1 Oct. 25, 2012

Related U.S. Application Data

(60) Provisional application No. 61/473,313, filed on Apr. 8, 2011.

(51) Int. Cl.
| | |
|---|---|
| *A61B 5/00* | (2006.01) |
| *G06T 7/20* | (2006.01) |
| *A61B 6/12* | (2006.01) |
| *A61B 6/00* | (2006.01) |
| *A61B 18/14* | (2006.01) |
| *A61B 18/00* | (2006.01) |

(52) U.S. Cl.
CPC ............. *A61B 5/7207* (2013.01); *A61B 6/12* (2013.01); *A61B 6/487* (2013.01); *A61B 6/5235* (2013.01); *G06T 7/2046* (2013.01); *G06T 7/2086* (2013.01); *A61B 18/1492* (2013.01); *A61B 2018/00357* (2013.01); *A61B 2018/00577* (2013.01); *A61B 2018/00982* (2013.01); *G06T 2207/10021* (2013.01); *G06T 2207/10121* (2013.01); *G06T 2207/30021* (2013.01)

(58) Field of Classification Search
CPC .................. A61B 2018/00982; A61B 5/7207; A61B 6/12; A61B 6/487; A61B 6/5235; G06T 2207/10021; G06T 2207/10121; G06T 2207/30021; G06T 7/2046; G06T 7/2086
See application file for complete search history.

(56) References Cited

U.S. PATENT DOCUMENTS

| | | | | |
|---|---|---|---|---|
| 2007/0270692 | A1* | 11/2007 | Barbu et al. | 600/431 |
| 2011/0230758 | A1* | 9/2011 | Eichler | 600/424 |
| 2013/0070995 | A1* | 3/2013 | Chou et al. | 382/131 |

OTHER PUBLICATIONS

D Sherknies et al. "3D Trajectory Assessment of an IVUS Transducer from Single-Plane Cineangiograms: a Phantom Study" IEEE Transactions on Biomedical Engineering Apr. 2005; 52(3):543-9.*
A Brost et al. "Real-time circumferential mapping catheter tracking for motion compensation in atrial fibrillation ablation procedures." Conference: Proceedings of SPIE Medical Imaging 2012: Image-Guided Procedures, Robotic Interventions, and Modeling.*
M Jourdain et al. "3D reconstruction of an IVUS transducer trajectory with a single view in cineangiography." SPIE 5747, Medical Imaging 2005: Image Processing, (Apr. 29, 2005).*

* cited by examiner

*Primary Examiner* — Amanda Lauritzen Moher

(57) ABSTRACT

A method for model based motion tracking of a catheter during an ablation procedure includes receiving a training series of biplanar fluoroscopic images of a catheter acquired under conditions that will be present during an ablation procedure, segmenting and processing the series of biplanar images to produce a distance transform image for each biplanar image at each acquisition time, minimizing, for each pair of biplanar images at each acquisition time, a cost function of the distance transform image for each pair of biplanar images to yield a translation parameter that provides a best fit for a model of the catheter to each pair of biplanar images at each acquisition time, and calculating an updated catheter model for each acquisition time from said translation parameter.

20 Claims, 20 Drawing Sheets

A sketch of the 3-D elliptical catheter model generation.

A sketch of the 3-D elliptical catheter model generation.

(a) Feature Types   (b) Classification and Regression Tree (CART)   (c) Cascade

Image processing on a fluoroscopic image.

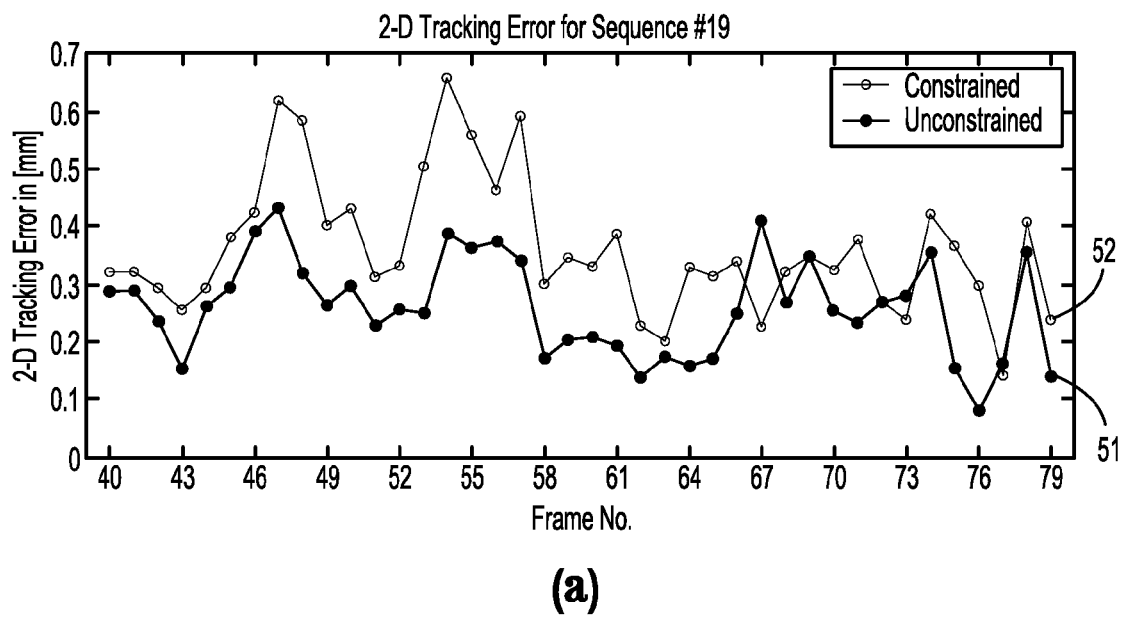
(a)
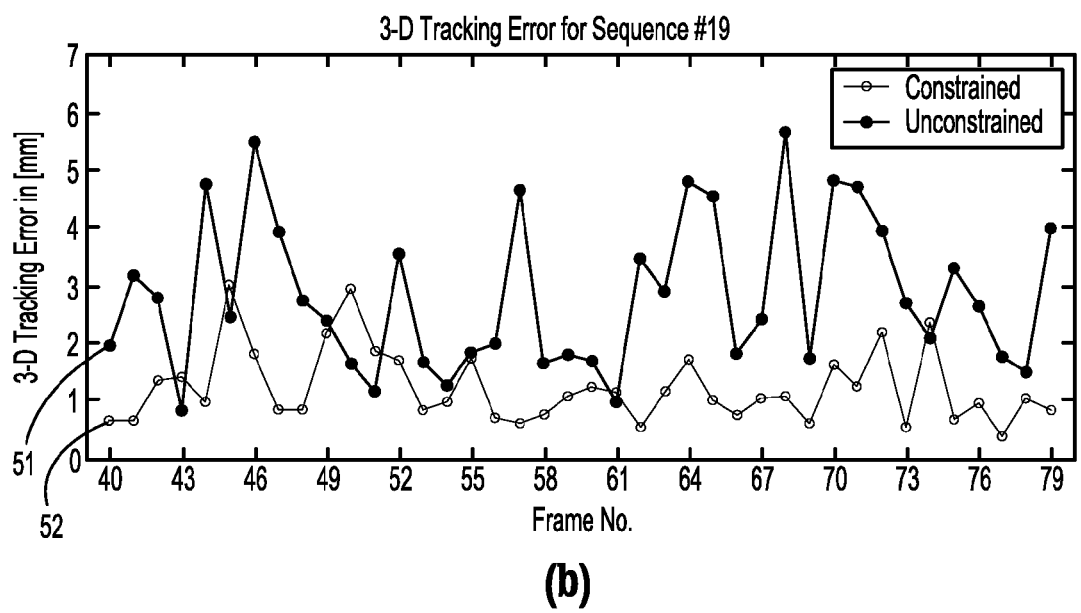
(b)
FIG. 5

Tracking error with respect to a noisy catheter model.

2-D Tracking error

Computational time

Segmentation results for different number of cascades.

TABLE I
RUNTIME OF ALGORITHM COMPONENTS

| Runtime | |
|---|---|
| Components | Runtime in [ms] |
| Segmentation | ~42 ms |
| Median | <1 ms |
| Skeletonization | ~47 ms |
| Distance Transform | <1 ms |
| Constrained Registration | ~17 ms |

(a)

TABLE II
COMPARISON BETWEEN SEVERAL METHODS ON MOTION
COMPENSATION USING 2-D/3-D REGISTRATION

| Method Comparison | | | |
|---|---|---|---|
| | Constrained | Unconstrained | Gold Standard |
| | Monoplane | Monoplane | Biplane |
| 2-D Error: | 0.6 mm | 0.6 mm | 0.8 mm |
| 3-D Error: | 1.6 mm | 3.2 mm | 0.7 mm |

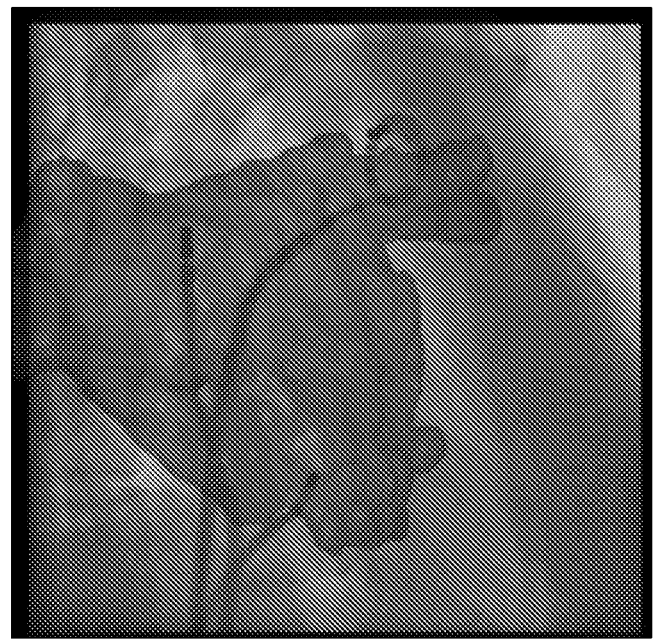
(a)
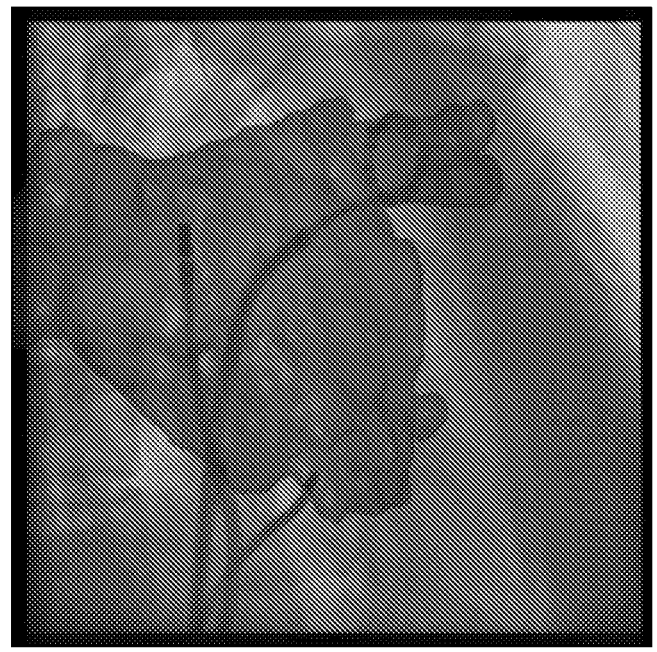
(b)
FIG. 14

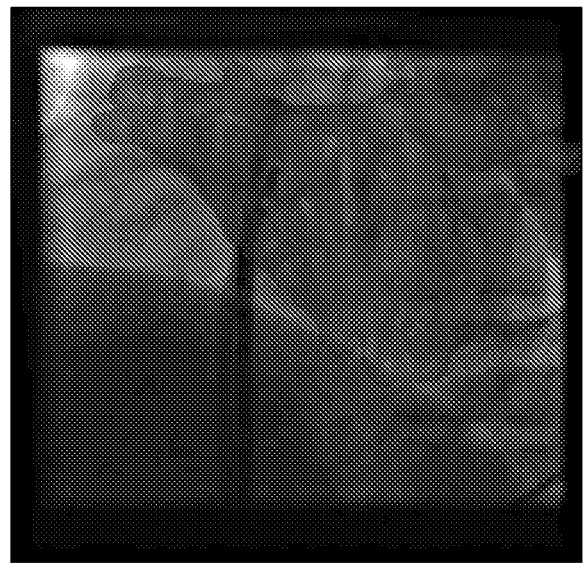
(a)
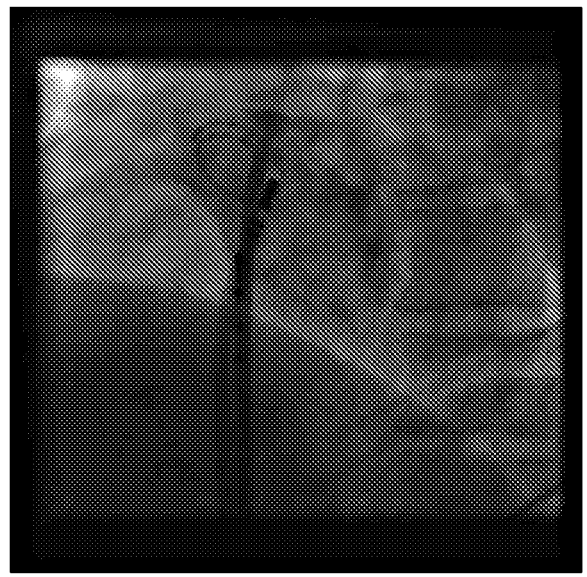
(b)
FIG. 15

1

CONSTRAINED REGISTRATION FOR MOTION COMPENSATION IN ATRIAL FIBRILLATION ABLATION PROCEDURES

CROSS REFERENCE TO RELATED UNITED STATES APPLICATIONS

This application claims priority from "Constrained Registration For Motion Compensation In Atrial Fibrillation Ablation Procedures", U.S. Provisional Application No. 61/473,313 of Liao, et al., filed Apr. 8, 2011, the contents of which are herein incorporated by reference in their entirety.

TECHNICAL FIELD

This disclosure is directed to methods for compensating motion in digitized fluoroscopy images used to guide catheter ablation procedures.

DISCUSSION OF THE RELATED ART

Atrial fibrillation (AFib) is the most common type of cardiac arrhythmia, and leads to an increased stroke risk for patients. Current treatments approaches include using radio-frequency ablations, in particular when drug therapy fails, and catheter ablation procedures that can be performed in electrophysiology (EP) labs equipped with modern C-arm X-ray systems. These devices often provide 3-D tomographic imaging to facilitate inter-procedural 3-D soft-tissue imaging. Electro-anatomic mapping systems are also available to visualize the catheter position in 3-D within a registered 3-D data set. While these systems can lower an X-ray dose, they add effort and cost to the procedure. In addition, mapping systems are virtual reality systems, and do not allow for instant confirmation of catheter positions under real-time X-ray. In some instances, they may even be off with respect to the underlying anatomy.

Augmented fluoroscopy, overlaying 2-D renderings obtained from either CT, MR, or C-arm CT 3-D data sets onto live fluoroscopic images, can facilitate more precise realtime catheter navigation and also reduce the X-ray dose. However, catheter navigation under augmented fluoroscopy is compromised by cardiac and respiratory motion. A first approach to handle this effect involved tracking commonly used circumferential mapping (CFM) catheters. As atrial fibrillation therapy takes place in the vicinity of the circumferential mapping catheter, tracking this catheter can be assumed to reliably capture the motion of the relevant treatment region if the device has been firmly positioned. Otherwise complete isolation of the pulmonary veins (PVs) may fail due to undetected residual PV-atrial electrical connections. Another previously proposed method involved a 3-D model of the catheter and applied an unconstrained 2-D/3-D registration approach to align the catheter model to biplane fluoroscopy images. An initial registration is performed manually to align the 3-D data to 2-D fluoroscopy with contrast injection showing the target organ. Once the 3-D overlay moves in sync with live fluoroscopic images, catheters can be guided to anatomical structures otherwise not visible under fluoroscopy with more confidence. A yet different approach for monoplane fluoroscopic imaging tracks a catheter only in 2-D and moves the overlay image on the live fluoroscopic images to be in sync with the cardiac and respiratory motion, observed by localizing the 2-D mapping catheter.

In EP labs equipped with biplane C-arm systems, often only one image plane is used at a time to reduce the radiation exposure to the patient. In this case, the above methods are not ideal, as they require re-initialization of the catheter model if the C-arm projection geometry changes during the intervention. Even though model re-initialization is not a very time consuming step, it does interrupt the workflow.

SUMMARY

Exemplary embodiments of the invention as described herein generally include methods and systems for 3-D motion compensation even if only monoplane X-ray images are available using a training phase that employs a biplane sequence to estimate a patient-specific motion model for the circumferential mapping catheter positioned at the pulmonary vein considered for ablation to obtain pulmonary vein isolation (PVI). A constrained model-based 2-D/3-D registration method is then used to track a circumferential mapping catheter.

According to an aspect of the invention, there is provided a method for model based motion tracking of a catheter during an ablation procedure including receiving a training series of biplanar fluoroscopic images of a catheter acquired under conditions that will be present during an ablation procedure, segmenting and processing the series of biplanar images to produce a distance transform image for each biplanar image at each acquisition time, minimizing, for each pair of biplanar images at each acquisition time, a first cost function of the distance transform image for each pair of biplanar images to yield a translation parameter that provides a best fit for a model of the catheter to each pair of biplanar images at each acquisition time, and calculating an updated catheter model for each acquisition time from the translation parameter.

According to a further aspect of the invention, the method includes calculating a model center for each updated catheter model, calculating a single motion vector from the model centers of the updated catheter models determining a viewing direction vector from a last row of a projection matrix from homogenous coordinates to a 3-D space, determining a search direction vector perpendicular to the viewing direction vector and the single motion vector, minimizing a second cost function of one distance transform image for each acquisition time, the cost function parameterized by the perpendicular search direction vector and the single motion vector to determine optimal coefficients of the perpendicular search direction vector and the single motion vector, and using the optimal coefficients with the perpendicular search direction vector and the single motion vector to update the catheter model at each acquisition time.

According to a further aspect of the invention, segmenting a biplanar image comprises using a cascade of weighted combinations of classification and regression trees (CARTs), where each CART is a weak classifier in which each node has a threshold associated with a feature that discriminates between a catheter and background and which partitions the feature space.

According to a further aspect of the invention, processing the series of biplanar images comprises smoothing segmentation results with a median filter, thinning the smoothed segmentation so that a catheter thickness need not be considered, and calculating for every background pixel in each image a distance to a closest object pixel to produce the distance transform image.

According to a further aspect of the invention, minimizing the first cost function comprises a multi-scale grid search that further comprises sub-sampling a search space and using a regions around a smallest cost function to initialize a search at a smaller scale.

According to a further aspect of the invention, the first cost function is $$\sum_i (I_{DT,A,t}(P_{A,t} \cdot T_t^u(r_t) \cdot m_{i,t}) + I_{DT,B,t}(P_{B,t} \cdot T_t^u(r_t) \cdot m_{i,t})),$$

where $P_{A,t}$ and $P_{B,t}$ are projection matrices for biplanar image planes A and B, $I_{DT,\,At}$, $I_{DT,\,Bt}$ are the distance transform images for each image in the pair of biplane images at time t, $$T_t^u(r) = \begin{pmatrix} 1 & 0 & 0 & r_{t,x} \\ 0 & 1 & 0 & r_{t,y} \\ 0 & 0 & 1 & r_{t,z} \\ 0 & 0 & 0 & 1 \end{pmatrix}$$

is a transformation matrix for the fluoroscopic images at time t with translation parameters $r_t = r_{t,x}, r_{t,y}, r_{t,z})^T$ and superscript u for 'unconstrained', respectively, and $m_{i,t}$ is the 3-D catheter model at time t, and the sum is over all points i in the catheter model.

According to a further aspect of the invention, the updated catheter model is calculated from $m_{i,t+1} = T_t^u(\hat{r}_t) \cdot m_{i,t}$ for all points i in the catheter model.

According to a further aspect of the invention, the model center for each updated catheter model is calculated from $$\bar{m}_t = \frac{1}{N} \sum_i m_{i,t},$$

where the sum is over all points i in the catheter model.

According to a further aspect of the invention, calculating the single motion vector comprises performing a principal component analysis over all images.

According to a further aspect of the invention, the second cost function is $$\sum_i I_{DT,t}(P \cdot T_c(\lambda, \mu) \cdot m_{i,t}),$$

where P is a projection matrix for one of the two biplanar images acquired for each time t, $I_{DT,t}$ is the distance transform image for the one biplanar image at each time t, where transformation matrix $$T_c(\lambda, \mu) = \begin{pmatrix} 1 & 0 & 0 & \lambda v_{p,x} + \mu v_{m,x} \\ 0 & 1 & 0 & \lambda v_{p,y} + \mu v_{m,y} \\ 0 & 0 & 1 & \lambda v_{p,z} + \mu v_{m,z} \\ 0 & 0 & 0 & 1 \end{pmatrix},$$

$\hat{\lambda}_t, \hat{\mu}_t$ are the optimal coefficients of the perpendicular search direction vector $v_p$ and the single motion vector $v_m$ with $v_p = (v_{p,x}, V_{p,y}, v_{p,z})^T$, $V_m = (v_{m,x}, v_{m,y}, v_{m,z})^T$ the index c is for 'constrained', and $m_{i,t}$ is the 3-D catheter model at time t, where the sum is over all points i in the catheter model.

According to a further aspect of the invention, the method includes weighting the transformation matrix over successive time steps as $$T_c'(\hat{\lambda}_t, \hat{\mu}_t) = \alpha T_c(\hat{\lambda}_t, \hat{\mu}_t) + (1-\alpha) T_c(\hat{\lambda}_{t-1}, \hat{\mu}_{t-1}) \text{ for } \alpha \in (0,1)$$

According to another aspect of the invention, there is provided a method for model based motion tracking of a catheter during an ablation procedure including receiving a training series of biplanar fluoroscopic images of a catheter acquired under conditions that will be present during an ablation procedure, providing a series of catheter models updated from a single initial catheter model to correspond to each pair of biplanar images in the training series, calculating a model center for each updated catheter model, calculating a single motion vector from the model centers of the updated catheter models, determining a viewing direction vector from a last row of a projection matrix from homogenous coordinates to a 3-D space, determining a search direction vector perpendicular to the viewing direction vector and the single motion vector, minimizing a first cost function of one distance transform image for each acquisition time, the cost function parameterized by the perpendicular search direction vector and the single motion vector to determine optimal coefficients of the perpendicular search direction vector and the single motion vector, and using the optimal coefficients with the perpendicular search direction vector and the single motion vector to update the catheter model at each acquisition time.

According to a further aspect of the invention, providing a series of catheter models includes segmenting and processing the series of biplanar images to produce a distance transform image for each biplanar image at each acquisition time, minimizing, for each pair of biplanar images at each acquisition time, a first cost function of the distance transform image for each pair of biplanar images to yield a translation parameter that provides a best fit of the initial catheter model 1 to each pair of biplanar images at each acquisition time, and calculating an updated catheter model for each acquisition time from the translation parameter.

According to another aspect of the invention, there is provided a non-transitory program storage device readable by a computer, tangibly embodying a program of instructions executed by the computer to perform the method steps for model based motion tracking of a catheter during an ablation procedure.

BRIEF DESCRIPTION OF THE DRAWINGS

FIG. 5(a) shows the 2-D tracking error for constrained and unconstrained approaches for each frame of a sequence, according to an embodiment of the invention.

FIG. 5(b) illustrates 3-D tracking error of the constrained and unconstrained approach for the same sequence shown in FIG. 5(a), according to an embodiment of the invention.

FIG. 13(a) is a table of results for the segmentation, median filtering, skeletonization, distance transform, and constrained registration, according to an embodiment of the invention.

FIG. 13(b) is a table of comparisons of several motion compensation methods utilizing 2-D/3-D registration, according to an embodiment of the invention.

FIGS. 14(a)-(b) illustrate a comparison showing the differences with and without motion compensation applied to the fluoroscopic overlay, according to an embodiment of the invention.

FIGS. 15(a)-(b) show a fluoroscopic image with a motion-compensated 3-D overlay compared to the original X-ray frame using contrast injection, according to an embodiment of the invention.

DETAILED DESCRIPTION OF EXEMPLARY EMBODIMENTS

Figure 1:
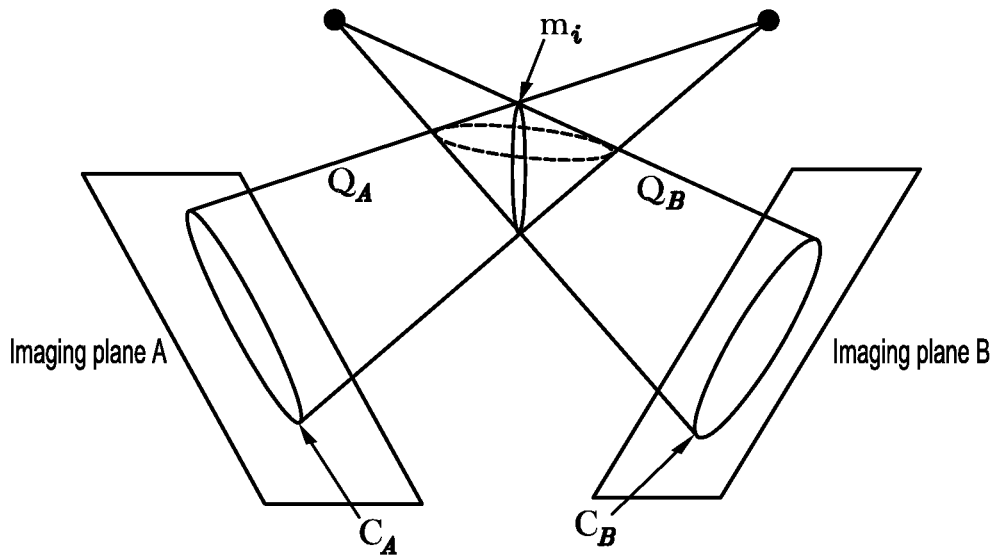
FIG. 1 illustrates an ellipse construction process according to an embodiment of the invention.

Exemplary embodiments of the invention as described herein generally include systems and methods for creating a patient-specific motion model and using the motion model to track a catheter during an ablation procedure. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-dimensional images and voxels for 3-dimensional images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the inventions are not limited to such images, and can be applied to images of any dimension, e.g., a 2-dimensional picture or a 3-dimensional volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

According to an embodiment of the invention, a constrained 2-D/3-D registration can be applied to perform motion compensation. An approach according to an embodiment of the invention is based on a 3-D catheter model and an estimated patient-specific motion model learned during a training phase. Set-up of the 3-D catheter model requires only a single biplane X-ray image, and the training phase estimates the motion of the CFM catheter at the PV using a biplane sequence in which the mapping catheter is tracked using an unconstrained 2-D/3-D registration. The principal motion axis is determined from the trajectory established during the tracking training phase. This axis is considered a patient-specific motion model. Since the main axis of the motion by itself is not sufficient to provide a good search space for a constrained registration, another axis is needed. According to an embodiment of the invention, a vector perpendicular to the viewing direction and the main axis is used, because the search region for the constrained registration can then be reduced to a 2-D search space, spanned by the principal axis and a vector parallel to the image plane. This allows tracking motion that is parallel to the image plane, and also capturing depth information with respect to the pre-acquired motion model. A constrained approach according to an embodiment of the invention can be simply stated as dimension reduction of the search space from 3-D to 2-D.

3-D Elliptical Catheter Model

A 3-D catheter model generation from two views using manually selected points as input is now summarized. A 3-D catheter model generation method according to an embodiment of the invention requires that points set on the catheter are displayed in a single biplane X-ray acquisition. Beyond that, this method puts no further restrictions on an operator, i.e., no special parts of the catheter need to be selected. Put differently, 2-D points $p_A$, $p_B \in R^2$ are selected on the elliptically-shaped part of the catheter in each image plane. The two image planes are denoted by A and B. Two-dimensional ellipses $C_A$, $C_B \in R^{3\times3}$ in the image planes are then fitted to these points using matrices of the form $$C_{A/B} = \begin{pmatrix} a & b & d \\ b & c & e \\ d & e & f \end{pmatrix},$$

with the coefficients of the fitted ellipse a, b, c, d, e, f∈R. If the 2-D points were on a perfect ellipse, the matrices would satisfy the following equations $$\tilde{p}_A^T C_A \tilde{p}_A = 0 \quad (1)$$

$$\tilde{p}_B^T C_B \tilde{p}_B = 0 \quad (2)$$

with the 2-D points $p_A$ and $p_B$ represented in homogeneous coordinates as $\tilde{p}_A = (p_A^T, 1)$ and $\tilde{p}_B = (p_B^T, 1)$. For ellipse fitting, at least six points are used, and ellipse fitting can be performed in a least-squares sense if more than six points are provided. A constraint $ac - b^2 > 0$ is used to ensure that the solutions for $C_A$ and $C_B$ are elliptical. After the ellipses in the image planes are fitted, ellipse reconstruction in 3-D can be performed by computing two 3-D cones $Q_A$, $Q_B \in R^{4\times4}$ using the projection matrices $P_A$, $P_B \in R^{3\times4}$. The cones are spanned from the cameras' optical centers to the ellipses on the image planes, as shown in FIG. 1. Two cones are computed as quadrics by $$Q_A = P_A^T C_A P_A, \quad (3)$$

$$Q_B = P_A^T C_B P_B, \quad (4)$$

The quadrics $Q_A$, $Q_B \in R^{4\times4}$ are of rank 3. Every intersection of a plane with one of the cones yields a valid solution of an ellipse in 3-D when projected onto the respective image plane. Given two cones, there are two possible solutions by calculating the two intersecting planes of the two 3-D cones. The two intersecting planes can be found by calculating a quadric $Q(\eta)$ from $Q(\eta) = Q_A + \eta Q_B$ such that the resulting $Q(\eta)$ is of rank 2. The solution is found by calculating the latent roots of $Q(\eta) = Q_A - \eta Q_B$, and the equations of the two intersecting planes are found by an eigenanalysis of the matrix $Q(\eta)$. Intersecting the 3-D cones with the two 3-D planes yields two possible solutions. The more circular solution of the two ellipses in 3-D is assumed to be the correct one, given the assumption that the pulmonary veins are tubularly shaped and that the circumferential mapping catheter is attached to the PV firmly. The 3-D model is denoted as $m_i = (m_{i,x}, m_{i,y}, m_{i,z}, 1)^T \in R^4$ in homogeneous coordinates with $i \in [1, N]$ and N is the number of model points. Experiments indicated that N=50 is sufficient to achieve good results. Increasing the number of model points did not lead to improved results. This step needs to be performed only once. FIG. 1 illustrates the ellipse construction process according to an embodiment of the invention, and depicts image planes A, B, 2-D ellipses $C_A$, $C_B$, cones $Q_A$, $Q_B$, and model points $m_i$.

Image Processing

Once a 3-D model of the catheter has been generated, only monoplane fluoroscopic imaging is needed for the remaining tasks of motion estimation and compensation. A method according to an embodiment of the invention does not require manual re-initialization of the catheter model when C-arm angulation changes, minimizing user interaction during interventions.

Catheter Segmentation

To segment a catheter in a fluoroscopic image, a 1024× 1024 pixel input image is cropped to a 400×400 pixel region-of-interest (ROI) around the projected center of the catheter model. A ROI size of 400×400 was chosen ensure that one can always find the circumferential mapping catheter in all images. Using a different ROI size, or to be more specific, a higher search range, would only affect the runtime. In the first frame, the position is known from the initialization step, and in all the subsequent frames, the tracking result from the previous frame is used.

Figure 2:
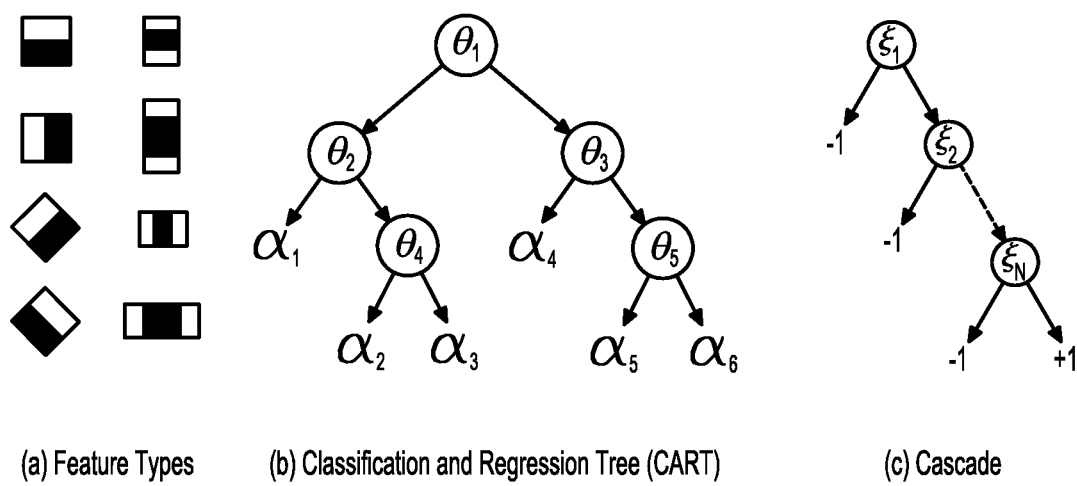
FIG. 2(a) depicts examples of Haar-like feature prototypes, according to an embodiment of the invention.
FIG. 2(b) depicts an example of a classification and regression tree (CART), according to an embodiment of the invention.
FIG. 2(c) depicts a classifier cascade of N stages of strong classifiers, according to an embodiment of the invention.

A catheter segmentation method according to an embodiment of the invention should be reliable and fast enough to allow motion estimation and compensation at the frame rate of the EP procedure, which typically ranges between 1 to 10 frames per second. According to an embodiment of the invention, a combination of Haar-like features and a cascade of boosted classifiers are used. AdaBoost in combination with Haar-like features has proven extremely successful in the field of real-time face detection. Haar-like features can calculate various patterns of intensity differences. Some features detect edges, whereas others focus on line-like structures and are useful for detecting thin objects such as the catheter. Examples of Haar-like feature prototypes are shown in FIG. 2(a). Actual features are generated by shifting and scaling the prototypes within a predefined window. Thus, contextual information around the center pixel is considered, which helps differentiate between the catheter and background structures. Haar-like features can be calculated efficiently using integral images.

Even for moderate window sizes, the number of generated features is large, about 40,000 for a 15×15 pixel window. The most suitable features for discriminating between catheter and background are selected by an AdaBoost algorithm and integrated into a classifier. The idea is to combine several weak classifiers, which only have to be slightly better than chance, to form a strong classifier. In the simplest case, a weak classifier amounts to a single feature and threshold. During training, weak classifiers are repeatedly evaluated on samples of a training set in which the catheter has been annotated. The classifier with a minimum classification error is added to a linear combination of weak classifiers until the overall error is below the desired threshold. After each iteration, the importance of individual samples is re-weighted to put more emphasis on misclassified samples for the next evaluation.

According to an embodiment of the invention, instead of single features and thresholds, classification and regression trees (CARTs) are used as weak classifiers. A CART is a small tree of fixed size. FIG. 2(b) depicts an example of a classification and regression tree (CART) with five feature nodes $\theta_1, \ldots, \theta_5$ and six leaves $\alpha_1, \ldots, \alpha_6$. At each node, a threshold associated with a feature partitions the feature space. Through this decomposition, flexibility is increased and objects with complex feature distributions can be handled. The value at the leaf represents the response of the classifier and indicates either catheter (positive) or background (negative). A CART having five splits, and thus six leaves, was found to perform best in experiments. When using a smaller number, the discriminative power of the tree may be too small, which in turn requires a larger number of trees for each stage. On the other hand, when using a larger number of splits, the tree may over fit to the training data, limiting its applicability to the unseen test data.

Several strong classifiers, each comprising a weighted combinations of CARTs, are organized into a cascade with N stages. FIG. 2(c) depicts a classifier cascade of N stages with strong classifiers $\xi_1, \ldots, \xi_N$. At each stage of the cascade, a sample is either rejected or passed on to the next stage. Only if the sample is accepted at the final stage is it assumed to belong to the object. Since many background pixels can be rejected at an early stage and since their number is large compared to the number of catheter pixels, this approaches reduces the computational cost when applying the cascade for catheter segmentation. During training, the focus is on maintaining a high true positive rate while successively reducing the false positive rate, either by adding more weak classifiers to a stage or by adding an entirely new stage. An embodiment of the invention aims for a positive rate of at least 99.5% and a false positive rate of not more than 50% per stage. A high true positive rate is required as a positive sample has to pass all the way down the cascade and must be accepted also by the last stage. When proceeding from stage to stage, a true positive rate of 0.995 per stage results in an overall true positive rate of $0.995^N$ for N stages. In case of N=4 stages, the expected true positive rate of the whole cascade is about 98%. For smaller true positive rates, the overall rate of the cascade would quickly decline. Setting the false positive rate to 0.5 per stage requires each stage of the cascade to halve the remaining number of false positives. In case of N=4 stages, the expected overall false positive rate is $0.5^N$=6.25%. With a higher false positive rate, more stages would be required to achieve an overall low false positive rate, whereas for a lower rate per stage, fewer stages but a more powerful strong classifier per stage would have to be trained. A gold-standard segmentation of the catheter was used for training.

Image Post-Processing

Different types of circumferential mapping catheters may be used for EP ablation purposes. These mapping catheters can differ in the number of electrodes as well as the thickness of the catheter. To ensure that a method according to an embodiment of the invention can handle a wide variety of catheters, post-processing is performed on the segmentation output from the learning-based catheter classifier. First, the catheter segmentation results are smoothed by a median filter. Experiments indicated that a 5×5 pixel kernel size yielded good results. Second, the smoothed segmentation is thinned so that the catheter thickness can be disregarded in the following registration step. Third, to obtain a smooth representation of the circumferential mapping catheter for subsequent registrations, the distance transform for the skeletonized image is calculated. The distance transform of an image calculates for every background pixel the distance to the closest object pixel. The resulting image is represented as $I_{DT}$.

Figure 3:
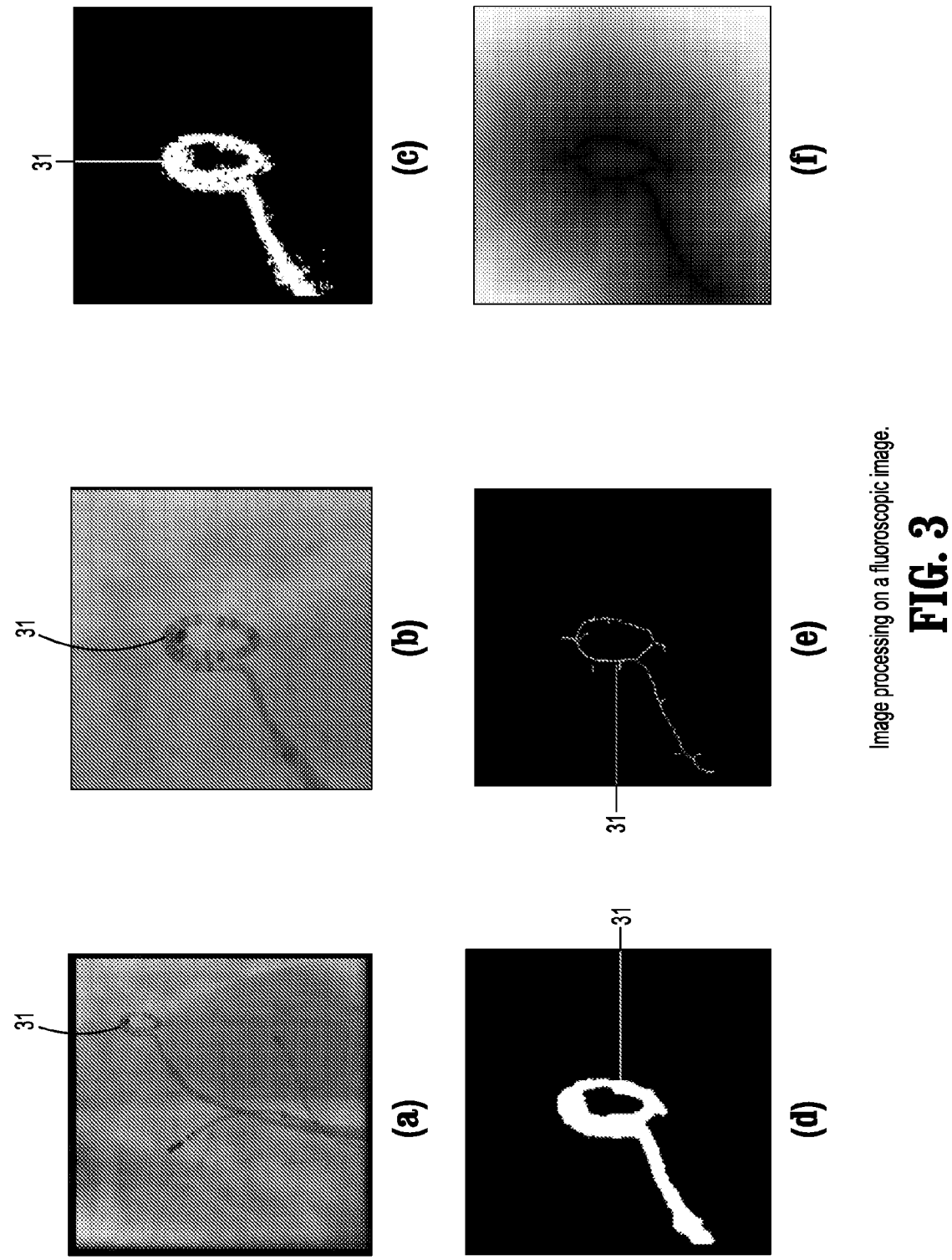
FIGS. 3(a)-(f) summarize the image segmentation and post-processing steps on a fluoroscopic image, according to an embodiment of the invention.

FIGS. 3(a)-(f) summarize the image processing steps on a fluoroscopic image, according to an embodiment of the invention. FIG. 3(a) shows an original fluoroscopic input image of a catheter 31. FIG. 3(b) depicts a cropped image of the catheter 31 around a region-of-interest. FIG. 3(c) shows a segmentation result of the catheter 31 of a boosted classifier cascade. FIG. 3(d) depicts a median filtered segmentation result of the catheter 31. FIG. 3(e) shows a skeletonized image of the catheter 31. FIG. 3(f) shows a distance transformed image $I_{DT}$.

Patient-Specific Motion Compensation

Next is presented a method according to an embodiment of the invention for the generation of a patient specific motion model. A short biplane sequence is used to generate 3-D samples of the position of the circumferential mapping catheter recorded during a training phase. The principal axis derived from the sample positions is taken as the main direction of PV motion. The motion model should be acquired in the same state (heart rate in sinus rhythm, arrhythmia) that will be present during the application of the motion model. Next, a constrained model-based 2-D/3-D registration is applied to track the circumferential mapping catheter in 3-D using monoplane fluoroscopy. To this end, the motion model estimated during the training phase limits the allowed motion to two directions. The first motion is parallel to the principal motion axis. The second allowed motion direction is parallel to the image plane, because the underlying motion vector is designed to be perpendicular to the principal axis and the viewing direction.

Motion-Model Generation

Figure 4:
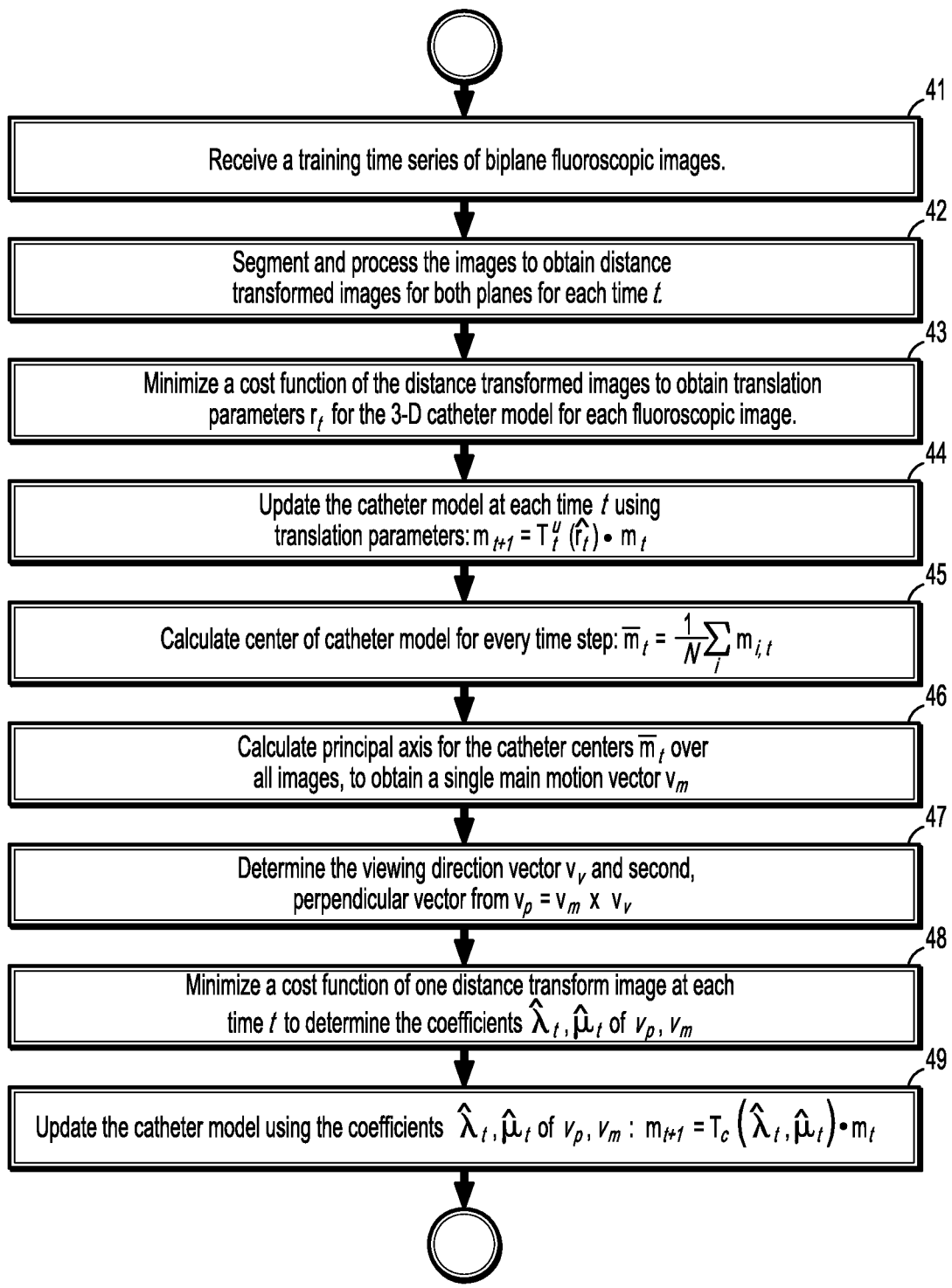
FIG. 4 is a flowchart of a method of creating a patient-specific motion model and using the motion model to track a catheter during an ablation procedure, according to an embodiment of the invention.

A motion model according to an embodiment of the invention is created by a 2-D/3-D registration of the previously generated 3-D catheter model to biplane fluoroscopic images acquired during a training phase. A flowchart of a method according to an embodiment of the invention of creating a patient-specific motion model and using the motion model to track a catheter during an ablation procedure is presented in FIG. 4. Referring to the flowchart, a method according to an embodiment of the invention begins at step 41 by receiving a training time series of biplane fluoroscopic images, acquired under the conditions that will be present during application of the motion model. The images are segmented and processed as described above at step 42, resulting in a distance transformed image for plane A, $I_{DT,A,t}$, and for plane B, $I_{DT,B,t}$, respectively, for each time t. A cost function of each pair of distance transformed images is minimized at step 43 to obtain translation parameters $r_t$ that provide a best fit of the 3-D catheter model to each 2-D fluoroscopic image. In this case, the transformation matrix for the fluoroscopic image at time t is written as $$T_t^u(r) = \begin{pmatrix} 1 & 0 & 0 & r_{t,x} \\ 0 & 1 & 0 & r_{t,y} \\ 0 & 0 & 1 & r_{t,z} \\ 0 & 0 & 0 & 1 \end{pmatrix}, \tag{5}$$

with translation parameters $r_t = (r_{t,x}, r_{t,y}, r_{t,z})^T$ and superscript u for 'unconstrained'. The cost function according to an embodiment of the invention can be formulated as $$\hat{r}_t = \arg\min_r \sum_i (I_{DT,A,t}(P_{A,t} \cdot T_t^u(r_t) \cdot m_{i,t}) + I_{DT,B,t}(P_{B,t} \cdot T_t^u(r_t) \cdot m_{i,t})), \tag{6}$$

with the projection matrices for image planes A and B, $P_{A,t}$ and $P_{B,t}$, respectively, as well as the 3-D catheter model, $m_{i,t}$, at time t. Minimization can be performed using a multi-scale grid search approach. The search space was sub-sampled and the region around the smallest cost function was used for a smaller search grid. The projection matrix used during the training phase tracking is not required to be one of the projection matrices used for model generation, i.e., the C-arm can be moved in between catheter model generation and the training phase. The same holds for the actual motion compensation. Given the parameters $\hat{r}$ found by the nearest-neighbor search, the catheter model can be updated at step 44 to $m_{i,t+1} \in R^4$ by $$\forall i: m_{i,t+1} = T_t^u(\hat{r}_t) \cdot m_{i,t}. \tag{7}$$

During the training phase, the same transformation $T_t^u(\hat{r}_t)$ can be applied to the 3-D volumetric data set that is used for image overlay. This way, a 3-D motion compensation can be shown during the training phase.

A patient specific motion model according to an embodiment of the invention is calculated from the circumferential mapping catheter positions. To this end, the catheter model for every time step is reduced to the center of the model at step 45 by $$\overline{m}_t = \frac{1}{N} \sum_i m_{i,t}. \qquad (8)$$

The principal axis for the catheter centers $\overline{m}_t$ is calculated at step 46 by a principal component analysis for all frames, to obtain a single main motion vector $v_m \in R^3$ with $\|v_m\|_2=1$. For a motion model according to an embodiment of the invention, only the principal axis is considered, as tracking inaccuracies during the training phase might produce outliers.

Motion Compensation by Model-Constrained Registration

Next, motion compensation according to an embodiment of the invention by model-constrained registration is introduced. The assumption of an approach according to an embodiment of the invention is that only monoplane fluoroscopic imaging is available. A constraint according to an embodiment of the invention is the reduction of the 3-D search space to a 2-D search space by introducing a second feasible motion vector that is perpendicular to the viewing direction and the principal motion vector. This results in a 2-D search plane for the catheter model that is semi-parallel to the image plane. The cost function is the distance transform $I_{DT}$ of the post-processed segmentation result. By using the main motion vector $v_m$, the 2-D search space also allows some depth estimation from a single X-ray view. Motion analyses of the left atrium have revealed that the dominant motion is in the anterior-posterior and superior-inferior directions. The degree of rotation is much less, possibly due to deformation of the left atrium. Physicians position their C-arms in standard viewing positions, and usually only angulations in the left-anterior-oblique (LAO), posterior-anterior (PA), or right-anterior-oblique (RAO) directions are used. Angulations towards cranial or caudal directions are, at least to the knowledge of the inventors, not common for EP procedures. If image acquisition is performed with the C-arm in an LAO, PA, or RAO position, most of the motion is captured, as the motion of the left atrium is parallel to the image plane.

Referring again to FIG. 4, to carry out constrained 2-D/3-D registration according to an embodiment of the invention, the viewing direction $v_v \in R^3$ with $\|v_v\|_2=1$ of the optical axis is determined at step 47 from the last row of the projection matrix $P \in R^{3 \times 4}$. The second vector required to estimate the second search direction, which is perpendicular to the viewing direction and the main motion axis, is given by $$v_p = v_m \times v_v. \qquad (9)$$

Any point on that plane can be represented by a linear combination of these two vectors $v_p$ and $v_m$. This translation can be rewritten in matrix notation as $$T_c(\lambda, \mu) = \begin{pmatrix} 1 & 0 & 0 & \lambda v_{p,x} + \mu v_{m,x} \\ 0 & 1 & 0 & \lambda v_{p,y} + \mu v_{m,y} \\ 0 & 0 & 1 & \lambda v_{p,z} + \mu v_{m,z} \\ 0 & 0 & 0 & 1 \end{pmatrix}, \qquad (10)$$

with $v_p = (v_{p,x}, v_{p,y}, v_{p,z})^T$ and $v_m = (v_{m,x}, v_{m,y}, V_{m,z})^T$ and the index c for 'constrained'. An objective function according to an embodiment of the invention for the constrained registration is then defined using the distance transformed images for image planes A or B, $I_{DT,A}$ or $I_{DT,B}$, respectively In the remainder of this section, the indices A and B are omitted, and P stands either for $P_A$ or $P_B$. The same holds for $I_{DT,t}$. A cost function according to an embodiment of the invention for the constrained registration can then be stated as:

$$\hat{\lambda}_t, \hat{\mu}_t = \arg \min_{\lambda, \mu} \sum_i I_{DT,i}(P \cdot T_c(\lambda, \mu) \cdot m_{i,t}). \qquad (11)$$

This cost function is minimized for each time step in the training series. Optimization of the cost function to determine the parameters $\hat{\lambda}_t, \hat{\mu}_t$ is performed at step 48 using a nearest-neighbor search, as for the training phase. Given the parameters $\hat{\lambda}_t, \hat{\mu}_t$, the catheter model can be updated at step 49 to $m_{i,t+1} \in R^4$ by $$\forall i : m_{i,t+1} = T_c(\hat{\lambda}_t, \hat{\mu}_t) \cdot m_{i,t}. \qquad (12)$$

The same transformation $T_c(\hat{\lambda}_t, \hat{\mu}_t)$ is then applied to the 3-D volumetric data set that is used to compute the image overlay by 2-D forward projection of the 3-D model based on the known projection geometry. This way, one can achieve 3-D motion compensation for monoplane fluoroscopic images.

According to other embodiments of the invention, additional processing can be performed on the transformation matrices $T_c(\hat{\lambda}_t, \hat{\mu}_t)$. Since the parameters $\hat{\lambda}_t, \hat{\mu}_t$ are calculated for each frame in the time series, the matrices $T_c(\hat{\lambda}_t, \hat{\mu}_t)$ are time dependent. According to an embodiment of the invention, one can weight the transformations over successive time steps: $T_c'(\hat{\lambda}_t, \hat{\mu}_t) = \alpha T_c(\hat{\lambda}_t, \hat{\mu}_t) + (1+\alpha)T_c(\hat{\lambda}_{t-1}, \hat{\mu}_{t-1})$ for $\alpha \in (0,1)$ exemplary, non-limiting value of a is 0.90.

Motion Compensation by Unconstrained Registration

According to an embodiment of the invention, the results of the constrained registration are compared to an unconstrained method that uses a full 3-D translation as a motion model. To this end, an unconstrained registration to a monoplane fluoroscopy image is performed. According to an embodiment of the invention, EQ. (6) can be adapted to the monoplane case by rewriting it as:

$$\hat{r}' = \arg \min_r \sum_i I_{DT,i}(P \cdot T_u(r) \cdot m_{i,t}). \qquad (13)$$

Motion compensation can be performed using $\hat{r}'$ to update the catheter model as in EQ. (7) and applying the same transformation to the 3-D data set used to generate the overlay images.

Evaluation and Results

Figure 6A:
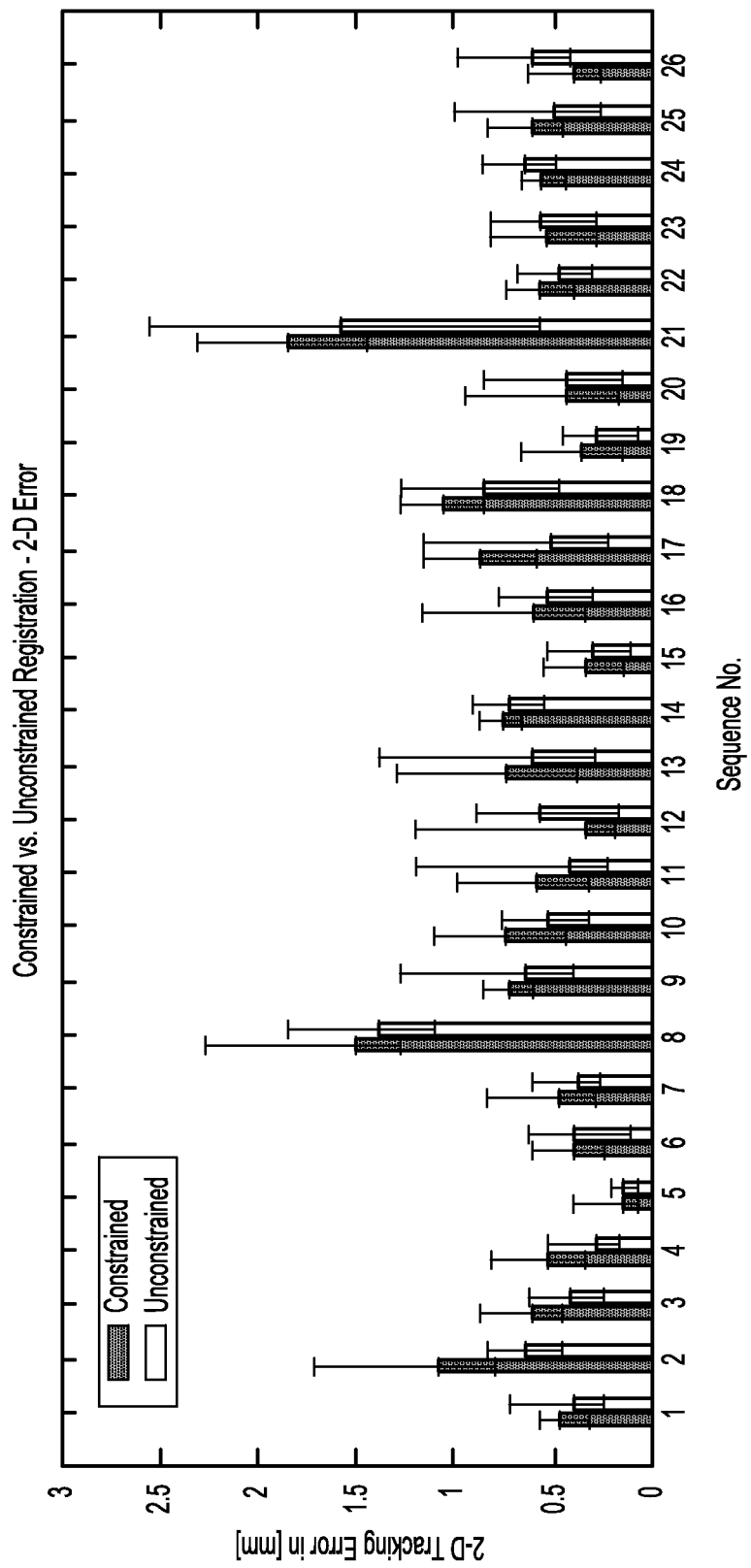
FIG. 6(a) illustrates a comparison of the 2-D tracking accuracy of constrained and unconstrained 2-D/3-D registration, according to an embodiment of the invention.
Figure 8:
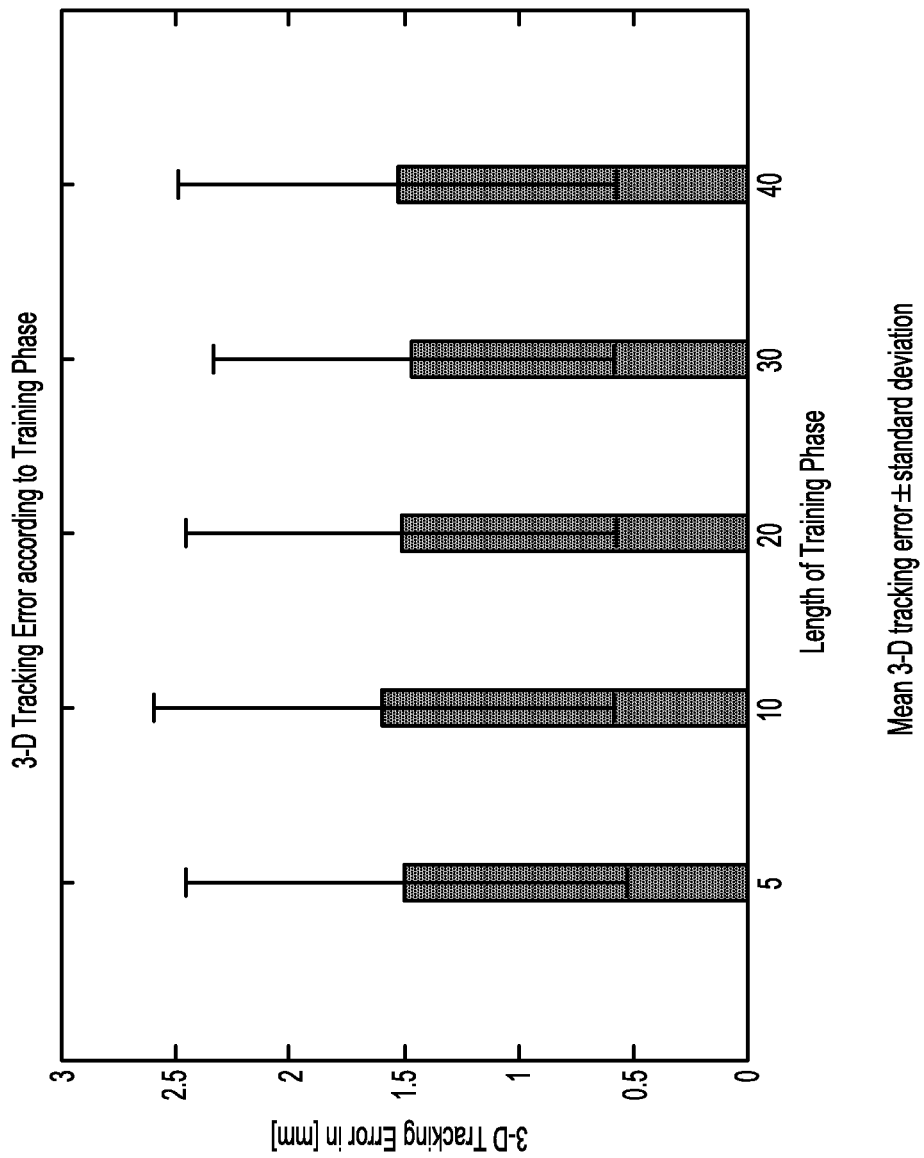
FIG. 8 depicts the mean 3-D tracking error±standard deviation calculated over three sequences, according to an embodiment of the invention.

Next, the performance of a motion-model constrained 2-D/3-D registration algorithm for motion compensation according to an embodiment of the invention is evaluated and the results are presented. The tracking accuracy of the constrained and unconstrained methods were calculated by comparison to a gold-standard segmentation. For evaluation, 13 clinical biplane sequences were available. Two different types of circumferential mapping catheters were encountered. One type was used in 11 biplane sequences, and a second type was used in the two other sequences. The fluoroscopic sequences were acquired during standard electrophysiology procedures. The circumferential mapping catheter was placed at the ostium of the pulmonary vein during image acquisition. The catheter is usually firmly placed to ensure a good wall contact. A suboptimal wall contact may lead to undetected residual PV-atrial electrical connections, and potentially to an incomplete pulmonary vein isolation. One gold-standard segmentation was available for each sequence, i.e., the catheter was segmented by one expert observer in each frame of the whole sequence. Data was acquired from six different patients at one clinical site. All X-ray sequences were recorded on an AXIOM Artis dBC biplane C-arm system (Siemens AG, Healthcare Sector, Forchheim, Germany). The training of the classifier was performed on a two-fold cross validation, i.e., the biplane sequence considered for evaluation was excluded from the training data set. For each sequence, a 3-D model was generated as described above. Then, a constrained method was evaluated by using each image plane of the biplane sequences independently. The frames used for the generation of the motion model were excluded from evaluation. For the unconstrained approach, the same frames were used for evaluation to arrive at comparable results. The constrained method used a training phase of 50% of the sequence. The shortest sequence available comprised 10 frames, and the longest 117. Individual sequences for training of the motion model were not available. To evaluate the influence of the number of frames used during the training phase, the three longest sequences available were used, comprising 79, 95 and 117 frames, respectively. The training phases for this evaluation were chosen to comprise 5, 10, 20, 30, and 40 frames, respectively. FIG. 8 depicts the mean 3-D tracking error±standard deviation calculated over three sequences with 79, 95, and 117 frames versus different frame numbers used during the training phase. A 2-D tracking error was obtained by calculating the average 2-D distance of the projected catheter model to the gold-standard segmentation. FIG. 6(a) illustrates a comparison of the 2-D tracking accuracy of the constrained and unconstrained 2-D/3-D registration. The unconstrained method achieved an average 2-D tracking error of 0.57 mm±0.31 mm. The performance of the constrained method differs little and yielded a 2-D tracking error of 0.55 mm±0.34 mm. The frames of the training phase were not included.

Figure 6B:
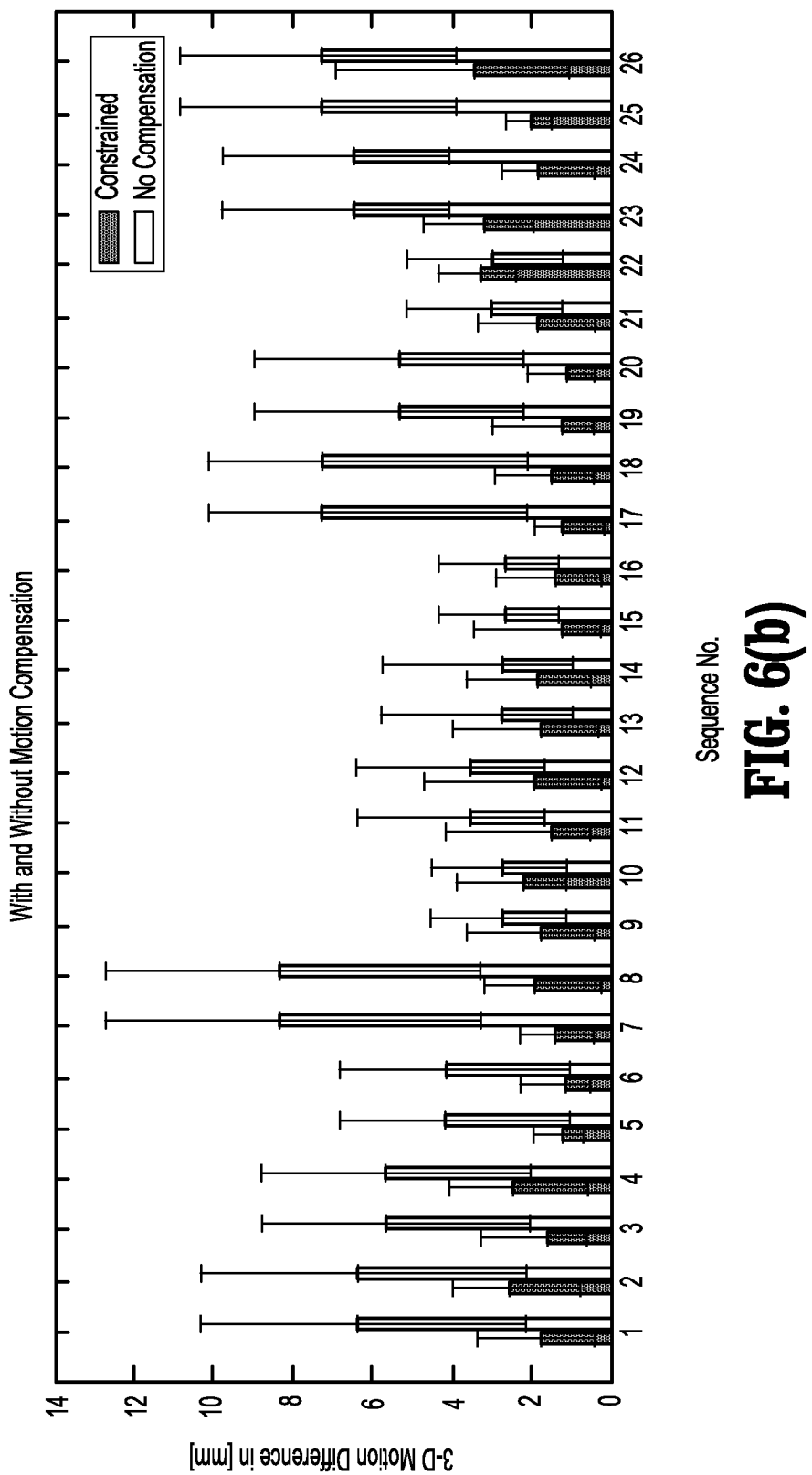
FIG. 6(b) compares 3-D error for constrained motion compensation versus no motion compensation, according to an embodiment of the invention.
Figure 6C:
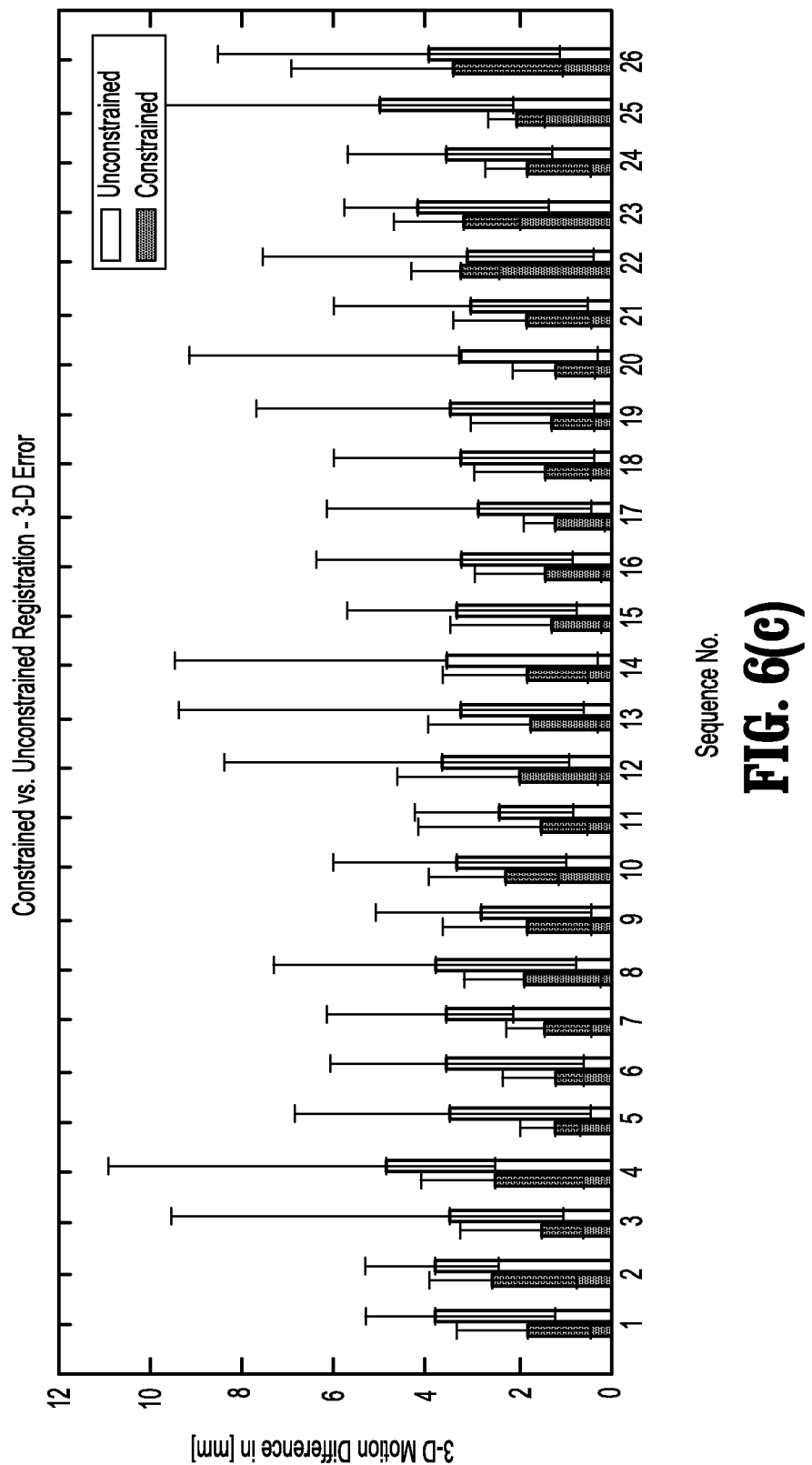
FIG. 6(c) compares 3-D motion compensation error obtained for constrained 2-D/3-D registration versus unconstrained 2-D/3-D registration, according to an embodiment of the invention.
Figure 6D:
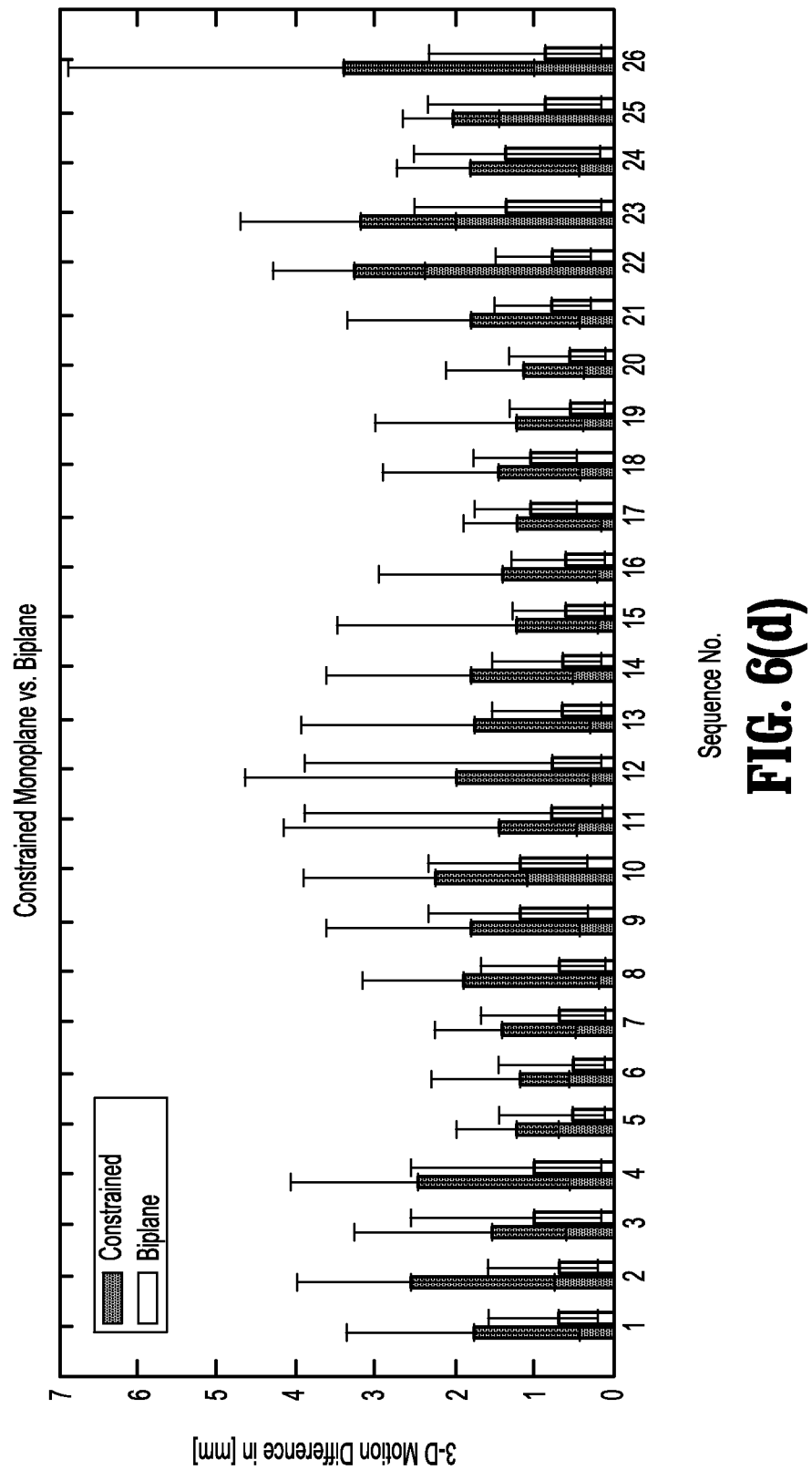
FIG. 6(d) illustrates a comparison of motion compensation between the constrained monoplane 2-D/3-D approach and the biplane approach, according to an embodiment of the invention.

Since motion estimation and compensation is performed in 3-D, and for each case there are biplane sequences to derive the ground truth position in 3-D, a 3-D error can be estimated as well. To this end, the tip of the circumferential mapping catheter was manually localized in 3-D by triangulation from two views. This can only be used as an estimation for the actual 3-D error. An accurate evaluation would require a high resolution 3-D data set for each time instant. Such data is unfortunately not available. The 3-D trajectories of the catheter tip were taken as the gold-standard for the observed 3-D motion. FIG. 6(b) compares 3-D error for constrained motion compensation versus no motion compensation, and FIG. 6(c) compares 3-D motion compensation error obtained for constrained 2-D/3-D registration versus unconstrained 2-D/3-D registration. For the 26 tested sequences, the observed motion was 4.5 mm±2.4 mm. The constrained motion compensation approach yielded a 3-D tracking error of 1.58 mm±0.95 mm. The unconstrained approach performed considerably worse with an average 3-D error of 3.21 mm±1.62 mm. Even though the constrained motion compensation method performed well, a gold-standard biplane method is still superior regarding the 3-D accuracy (0.7 mm±0.4 mm). However, its better accuracy comes at the cost of increased X-ray dose. FIG. 6(d) illustrates a comparison of motion compensation between the constrained monoplane 2-D/3-D approach and the biplane approach. In addition, a comparison of several motion compensation methods utilizing 2-D/3-D registration is given in Table II, shown in FIG. 13(b). This includes the proposed constrained method, the unconstrained method, as well as the gold standard reference biplane method.

Figure 9:
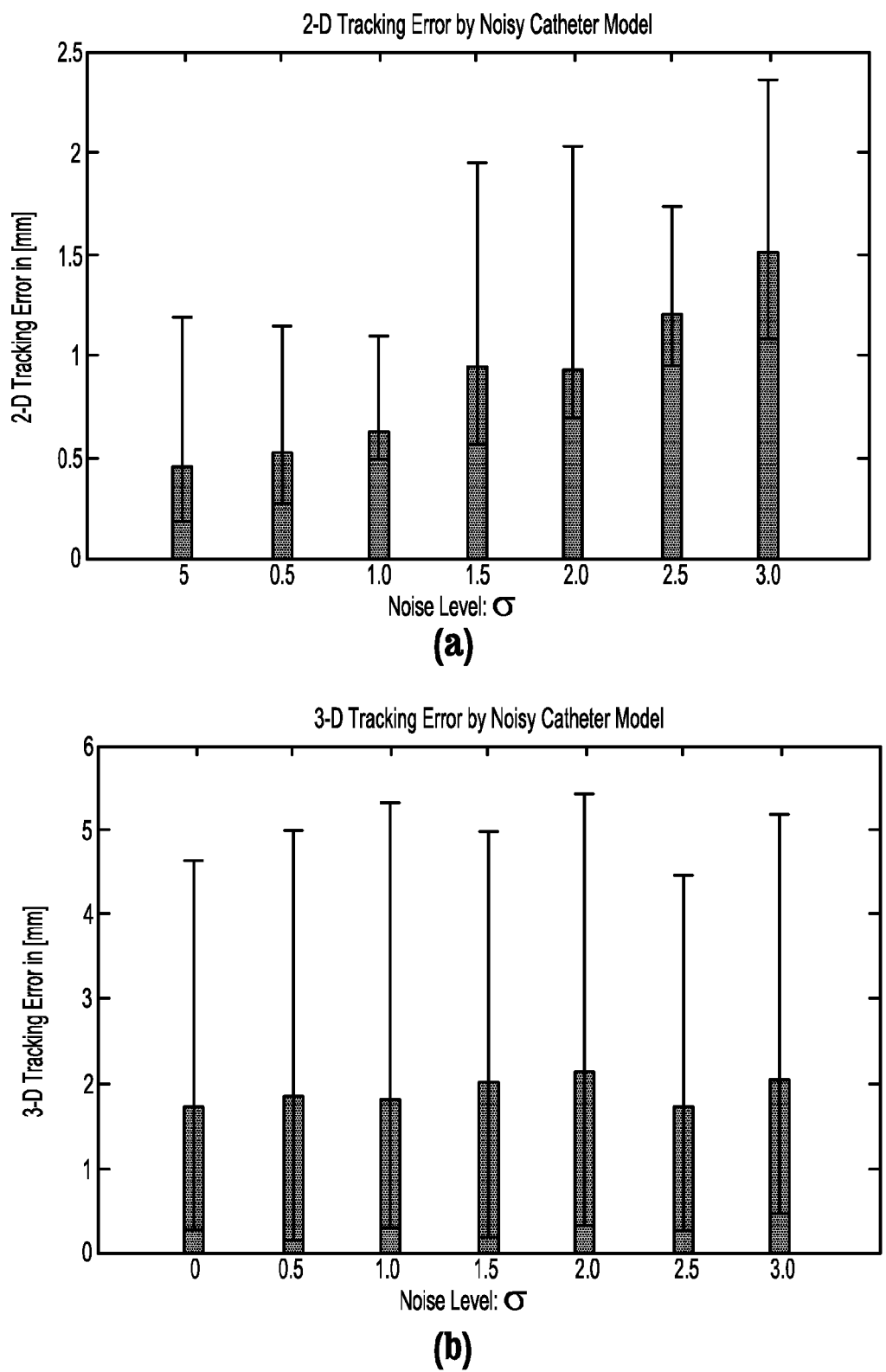
FIGS. 9(a)-(b) show 2-D and 3D tracking error results, respectively, according to an embodiment of the invention.

As drift is an often discussed issue when evaluating tracking methods, tracking error over time was also considered. This question is especially interesting, as only one previous frame is considered when tracking the current frame. In particular, the tracking result of the previous frame is used for cropping the region-of-interest in the current frame. Apart from that, all frames are treated independently. For example, the 2-D tracking error for constrained 52 and unconstrained 51 approaches for each frame of sequence #19 is given in FIG. 5(a), and FIG. 5(b) illustrates 3-D tracking error of the constrained 52 and unconstrained 51 approach for the same sequence. Both the unconstrained and the constrained approaches achieved comparable results with the constrained method yielding a slightly higher 2-D error. Specifically, in this particular sequence, the 2-D tracking error was 0.36 mm±0.12 mm for the constrained method and 0.26 mm±0.09 mm for the unconstrained approach, respectively. The constrained method yielded a 3-D tracking error of 1.24 mm±0.64 mm, in comparison to the 3-D tracking error of 2.83 mm±1.34 mm for the unconstrained method. Neither method suffered from drifting issues, suggesting that a model-based 2-D/3-D registration using a pre-generated 3-D catheter model according to an embodiment of the invention is robust with respect to sporadic tracking errors. To further evaluate how robust a method according to an embodiment of the invention behaves against catheter model errors, the longest available sequence was chosen and the respective 3-D model was disturbed by Gaussian noise with different standard deviations. Afterwards, tracking was performed and evaluated. FIG. 9(a) shows the 2-D tracking error results, and FIG. 9(b) shows the 3-D tracking error results. It took a standard deviation of more than 3.0 mm to trigger tracking failures. And even then, the failures occurred in one image plane, demonstrating that a good view on an inaccurate catheter model may be able to work around this effect, although only up to a certain degree of noise, of course.

Figure 7A:
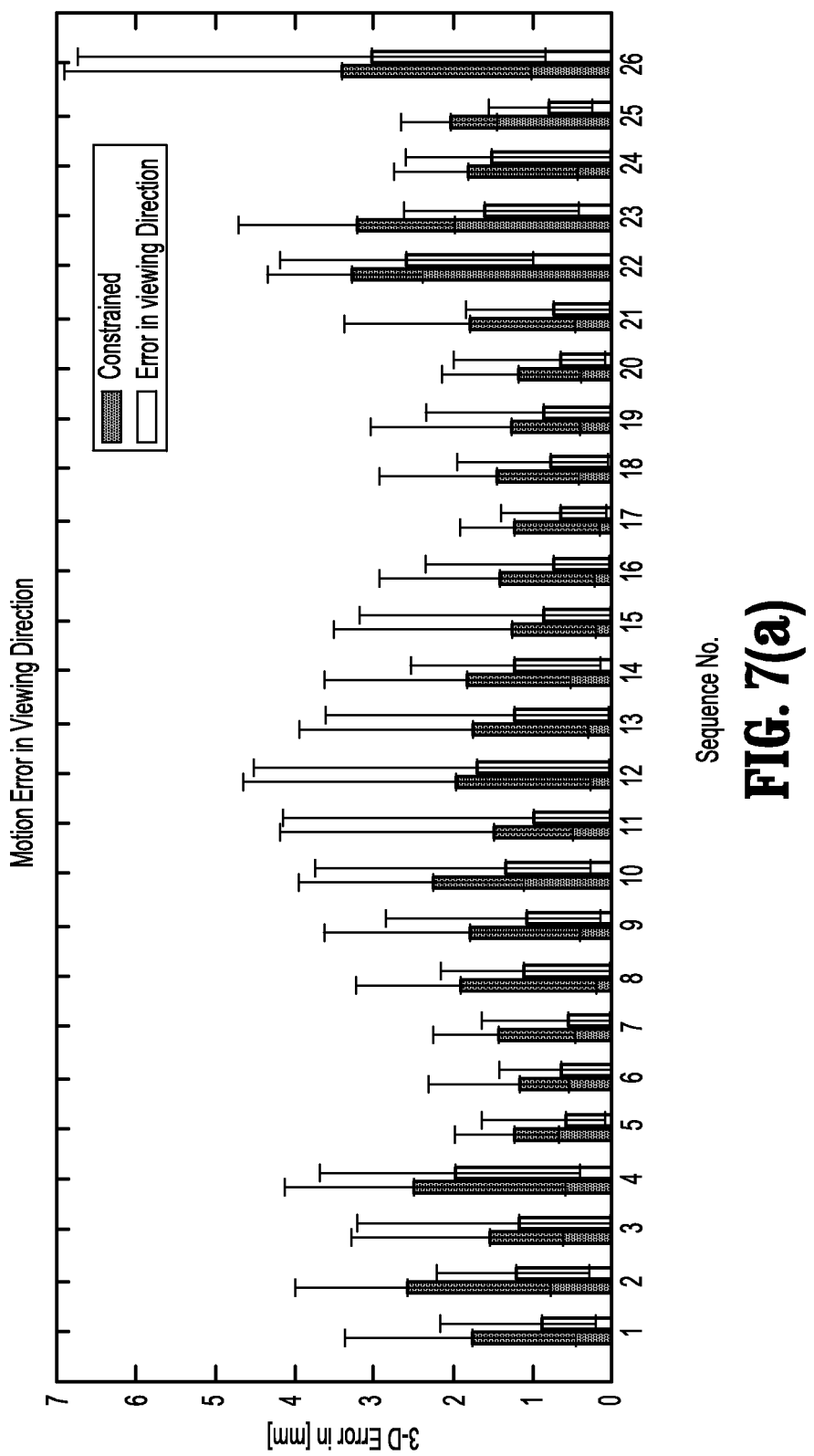
FIGS. 7(a)-(b) illustrate the motion compensation error along the viewing direction of the constrained and unconstrained methods, respectively, according to an embodiment of the invention.
Figure 7B:
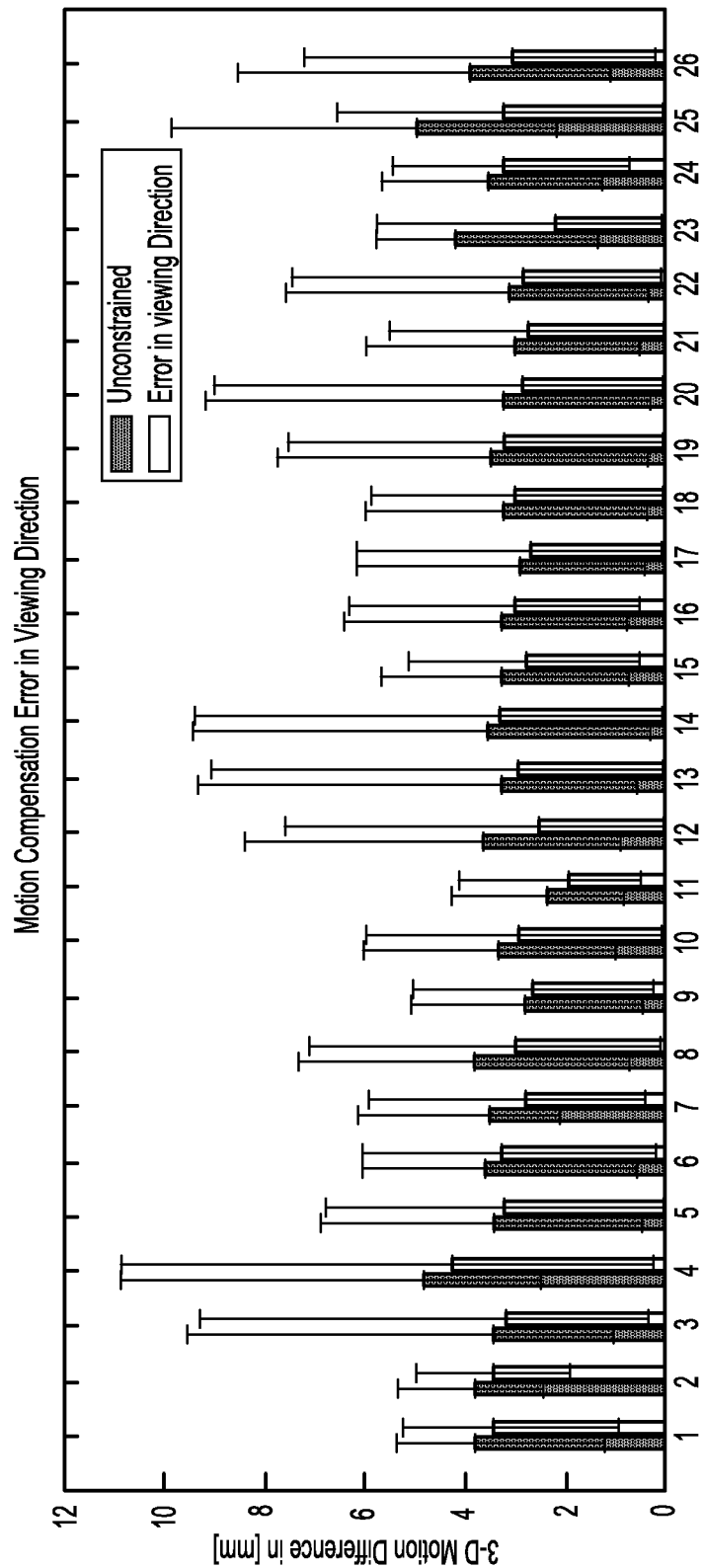

The error along the viewing direction was also computed. Since this direction is excluded in the search space for the constrained method, the error along the viewing direction was the largest among all directions, averaging at 1.03 mm±0.94 mm. However, the unconstrained method also had its largest error along the viewing direction with an average of 2.99 mm±0.43 mm FIG. 7(a) illustrates the motion compensation error along the viewing direction of the constrained method, and FIG. 7(b) illustrates the same graph for the unconstrained method. This confirms that estimating object depth from monoplane fluoroscopy is challenging, and also confirms that the constrained approach is a reasonable choice for tracking a mapping catheter put in place firmly at a pulmonary vein ostium.

Figure 10:
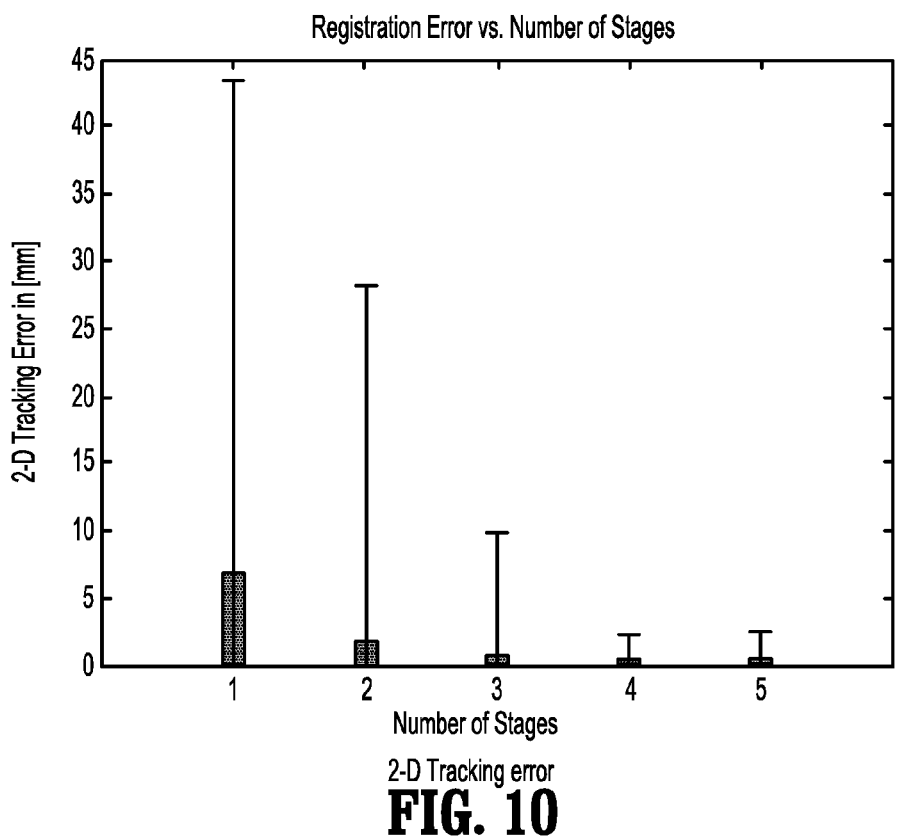
FIG. 10 illustrates 2-D tracking error versus the number of stages in a boosted classifier cascade, according to an embodiment of the invention.

A method according to an embodiment of the invention uses a boosted classifier cascade. To evaluate how many stages in the cascade are needed for achieving good motion compensation results, an experiment using a constrained method according to an embodiment of the invention was performed. FIG. 10 illustrates 2-D tracking error versus the number of stages in the boosted classifier cascade. With an increasing number of stages, the tracking accuracy improved. Using less than three stages yielded unsuccessful tracking results on the data set. According to the results and considering the fact that by using too many stages, one runs the risk of overfitting the model to the noise in the training data, an embodiment of the invention uses 4 stages in the cascade. All results shown herein were obtained using 4 stages.

Figure 11:
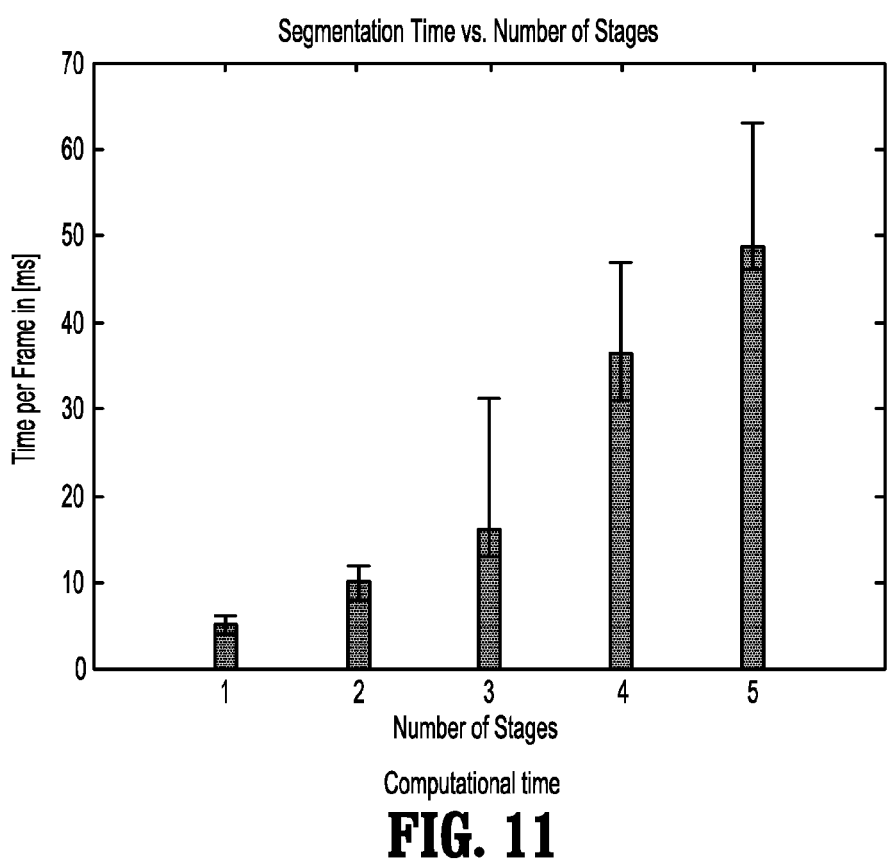
FIG. 11 shows the results of the computational time of the catheter segmentation versus the number of stages in the boosted classifier cascade, according to an embodiment of the invention.
Figure 12:
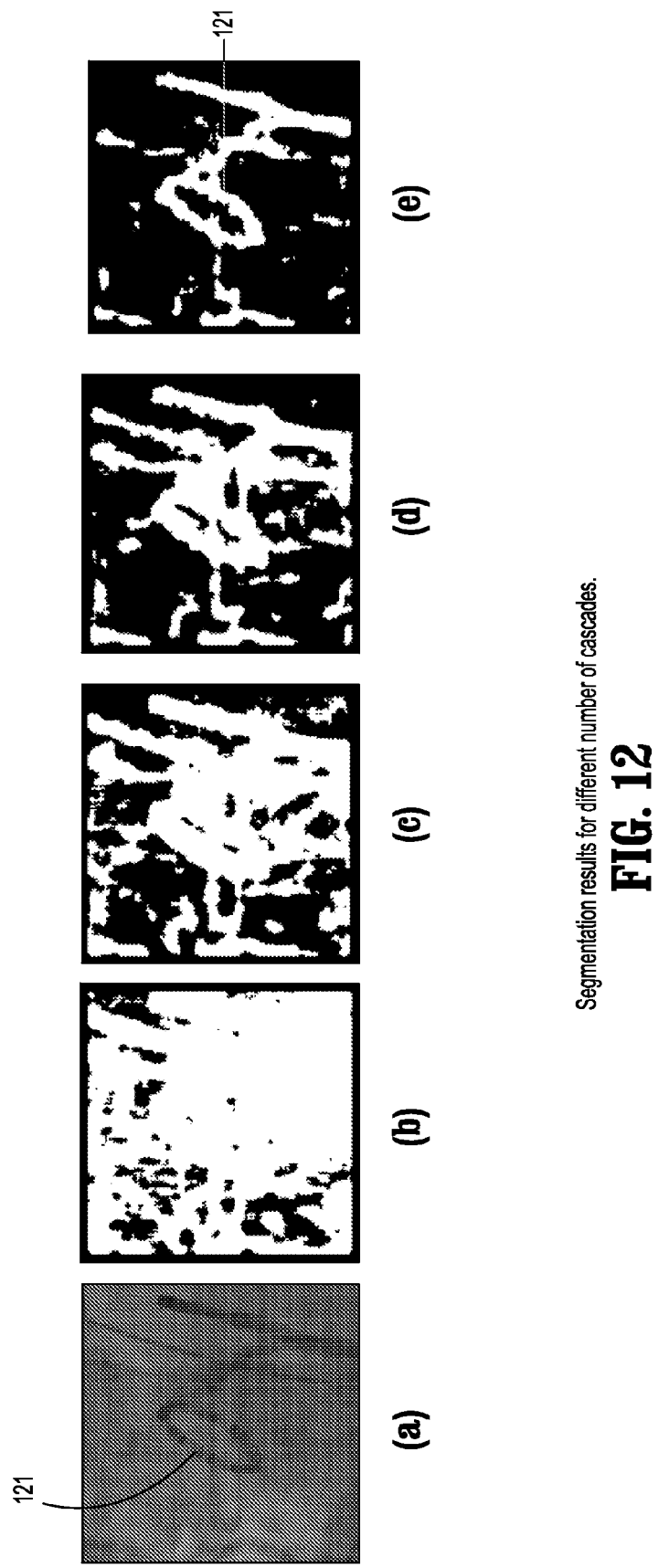
FIGS. 12(a)-(e) shows examples of how segmentation results depend on the number of stages used for classification, according to an embodiment of the invention.

The number of stages used in the cascade can also be addressed by looking at the time required to estimate the motion for one frame. Fast and accurate methods are desired for interventional applications. The time in ms was measured for each frame and the average, the minimum and the maximum were calculated. The results of the computational time of the catheter segmentation versus the number of stages in the boosted classifier cascade are shown in FIG. 11. An example for segmentation results depending on the number of stages used for classification is shown in FIGS. 12(a)-(e). The segmentation results shown here are smoothed by a median filter. FIG. 12(a) shows a cropped image used for segmentation, with a catheter 121. FIG. 12(b) shows a segmentation result using one stage in the cascade. FIG. 12(c) shows a segmentation result using two stages. FIG. 12(d) shows a segmentation result using three stages, and FIG. 12(e) shows a segmentation result 121 using four stages.

Besides the runtime of the classification, the runtime of all components of our presented algorithm are also of interest. Results for the segmentation, median filtering, skeletonization, distance transform, and constrained registration are presented in Table I, shown in FIG. 13(a). The time measurements were performed on an Intel Xeon E5440 at 2.83 GHz.

The initialization of the catheter model used for motion compensation in a method according to an embodiment of the invention is required only once. A 2-D/3-D registration according to an embodiment of the invention incorporates the projection matrix, so no model reinitialization is required if the viewing direction of a C-arm is changed. Although model re-initialization is usually not time consuming, it does interrupt the workflow because of manual interaction involving the user. In fact, while the catheter model can be calculated in less than 55 ms on a PC platform, user feedback needed for model initialization carries the risk of slowing the workflow.

Figure 16:
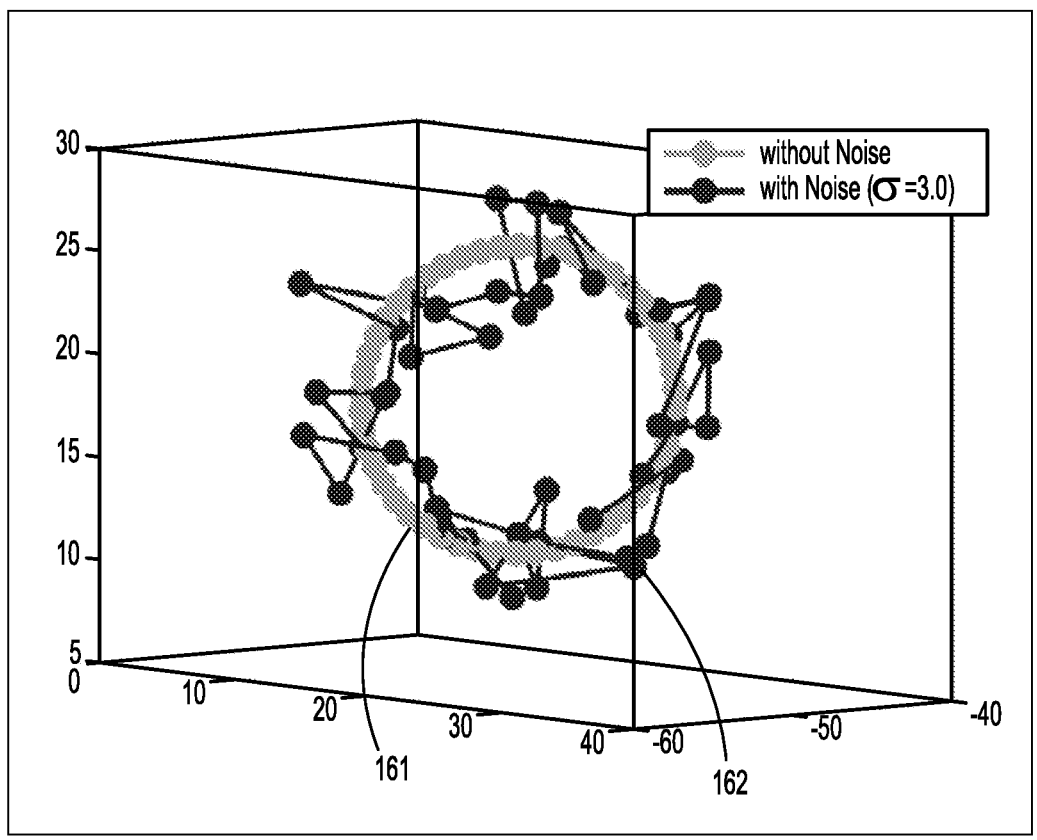
FIG. 16 depicts a catheter model and a catheter model disturbed by noise, according to an embodiment of the invention.

During the experiments, it was found that a catheter model of 50 points yielded good results. Increasing the number of model points did not improve tracking accuracy. FIG. 16 depicts such a catheter model 161 along with a catheter model disturbed by noise 162. The noisy catheter model was disturbed by Gaussian noise with zero mean and a standard deviation of 3.0 mm.

A method according to an embodiment of the invention relies on a constrained 2-D/3-D registration involving a 3-D catheter model as well as a motion model, and can capture the relevant motion at the site of ablation and take it into account real-time. Since an approach according to an embodiment of the invention uses a 3-D catheter model, re-initialization after repositioning the C-arm can be avoided. However, the reconstruction of the 3-D catheter model requires at least two views in the same cardiac cycle and breathing phase.

The computation of the motion model requires a training phase. In clinical practice, the training phase could be included into the workflow. At the beginning of each AFib ablation procedure, the signals at the PVs are documented and the correct position of the circumferential mapping catheter is verified by contrast injection and, if available, using a short biplane sequence. This sequence could be sufficient to initialize a motion model according to an embodiment of the invention. As four pulmonary veins are typically ablated during a procedure, four individual motion models, one for each PV, may need to be trained. Evaluating the 3-D tracking error with respect to number of frames used during the training phase indicated that a method according to an embodiment of the invention is insensitive to the length of the training phase, as shown in FIG. 8. Even though a short sequence may be sufficient to estimate the principle direction of the motion, a full breathing cycle can be used for best results. This could be done with a consciously sedated patient.

A method according to an embodiment of the invention can achieve a 3-D accuracy of about 1.6 mm. However, to reduce the 3-D error, one could employ simultaneous biplane imaging, which comes at the cost of a higher dose for the patient and the medical staff.

A method according to an embodiment of the invention cannot take into account motion along the viewing direction because depth information cannot be reliably estimated from monoplane projection images. Using an unconstrained approach, the 3-D error remains high, especially along the viewing direction, as shown in FIGS. 7(a)-(b). Depth correction could be performed by analyzing the width of the object. But this requires a perfect segmentation of the catheter from the fluoroscopy views, which is challenging for low-dose X-ray images. In addition, one would also need to know the exact dimensions of the catheter in 3-D, i.e., its diameter and thickness. Any noise or inaccuracy in the 2-D segmentation or the 3-D model would deteriorate the accuracy of depth estimation. Even if the depth information could be accurately estimated, the effect would probably not be visible because the size of the overlay would only change slightly. Due to a motion model, a method according to an embodiment of the invention does not need an explicit depth-estimation step. Significant motion in the X-ray view direction can be captured by the main motion axis.

Figure 17:
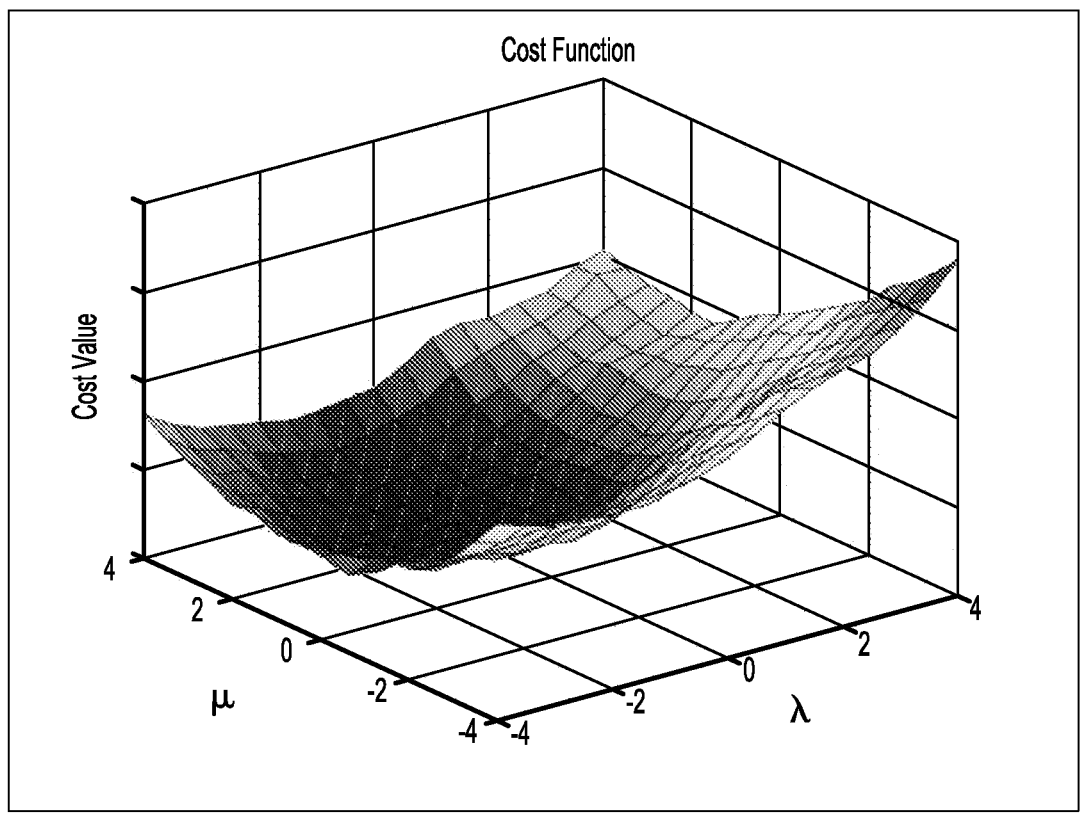
FIG. 17 is a visualization of a cost function for one frame in a small area around an optimum, according to an embodiment of the invention.

The distance transform provides the main input for the cost function. As long as only one circumferential mapping catheter appears in the image, there is only one global optimum for the cost function. A multi-scale grid-search approach according to an embodiment of the invention did not detect any local optima. If multiple elliptical shaped catheters were used, local optima would appear and an optimization strategy according to an embodiment of the invention could detect one of these. A visualization of a cost function for one frame in a small area around an optimum is shown in FIG. 17. The global optimum is at $\mu=1.0$ mm and $\lambda=-0.5$ mm.

A method according to an embodiment of the invention is purely image driven, and can be extended to learn the motion difference between the circumferential mapping and the coronary sinus (CS) catheter. The same idea could be applied to using the diaphragm for motion compensation. Embodiments of the invention for motion estimation rely on the assumption that the circumferential mapping catheter is thinly placed at the PV where ablation takes place. If the mapping catheter floated freely within the left atrium, one could not get a reliable motion estimate. In such a case, an additional motion analysis stage could detect the free motion.

To further improve the accuracy, other methods such as probabilistic boosting trees or random forests can be used for catheter segmentation. For a higher efficiency, a different skeletonization method other than the thinning algorithm could be used. Since motion compensation for AFib ablation procedures should be usable within an interventional setup, near real-time performance is desirable. In this context, real-time is regarded as the frame rate that is used for image acquisition during the intervention. AFib ablation procedures are lengthy procedures, and fluoroscopy times often accumulate to more than 30 minutes. This is why physicians try to reduce dose, e.g., by lowering the acquisition frame rates. One reason for the long fluoroscopy times is the complexity encountered when trying to isolate the pulmonary veins. Embodiments of the invention can shorten the procedure time by offering navigation based on fluoroscopy overlay images.

A comparison showing the difference with and without motion compensation applied to the fluoroscopic overlay is presented in FIGS. 14(a)-(b). FIG. 14(a) depicts one frame of sequence 17 without motion compensation, while FIG. 14(b) shows the same frame of sequence 17 with motion compensation. FIGS. 15(a)-(b) show a fluoroscopic image with a motion-compensated 3-D overlay compared to the original X-ray frame using contrast injection. FIG. 15(a) shows one motion compensated frame of one sequence with 3-D overlay during contrast injection close to one pulmonary vein, while FIG. 15(b) shows the same frame without the 3-D overlay. In a clinical setup, a physician working on a biplane system is likely to alternate between the two X-ray image planes. A method according to an embodiment of the invention is usable in such situations.

System Implementations

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 18:
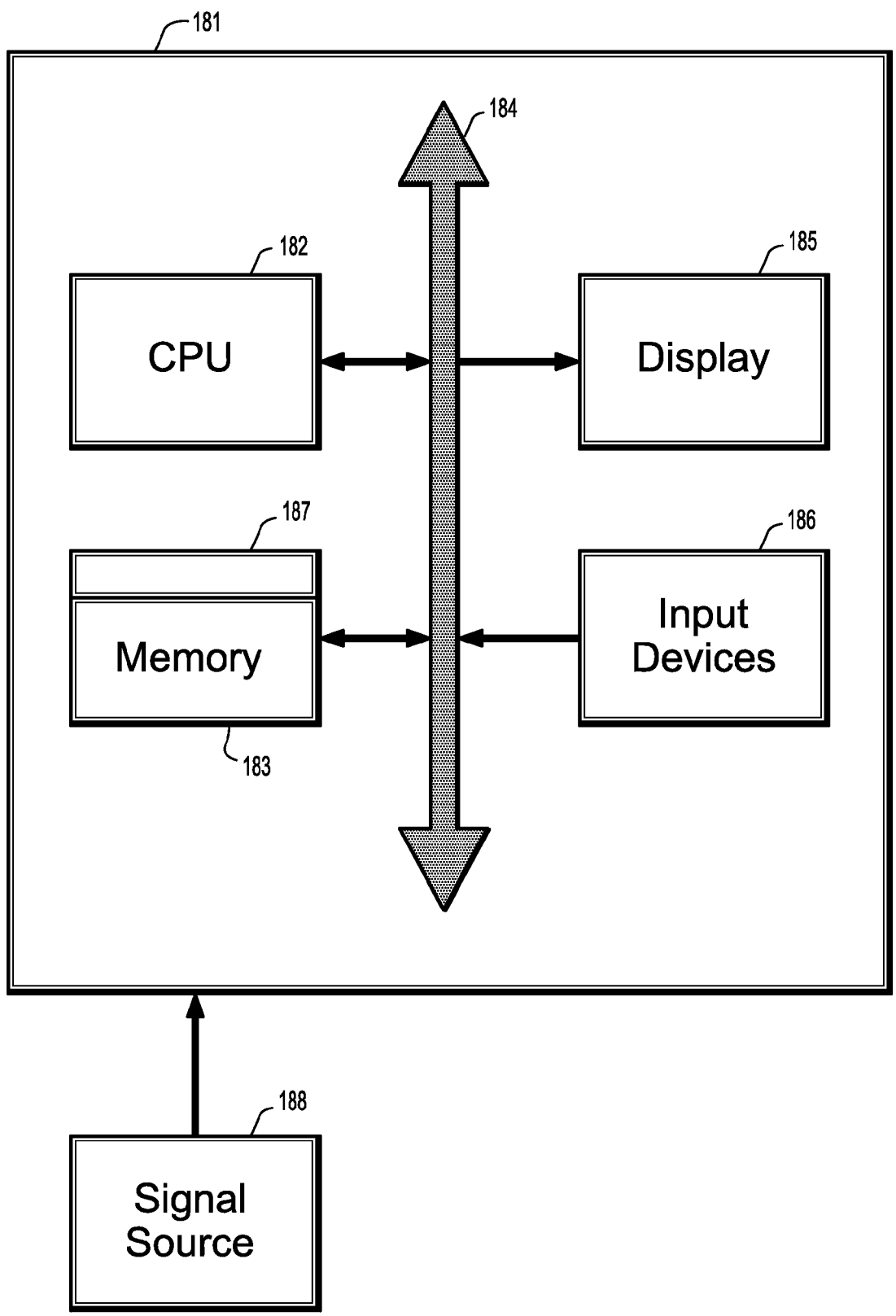
FIG. 18 is a block diagram of an exemplary computer system for implementing a method of creating a patient-specific motion model and using the motion model to track a catheter during an ablation procedure, according to an embodiment of the invention.

FIG. 18 is a block diagram of an exemplary computer system for implementing a method of creating a patient-specific motion model and using the motion model to track a catheter during an ablation procedure according to an embodiment of the invention. Referring now to FIG. 18, a computer system 181 for implementing the present invention can comprise, inter alia, a central processing unit (CPU) 182, a memory 183 and an input/output (I/O) interface 184. The computer system 181 is generally coupled through the I/O interface 184 to a display 185 and various input devices 186 such as a mouse and a keyboard. The support circuits can include circuits such as cache, power supplies, clock circuits, and a communication bus. The memory 183 can include random access memory (RAM), read only memory (ROM), disk drive, tape drive, etc., or a combinations thereof. The present invention can be implemented as a routine 187 that is stored in memory 183 and executed by the CPU 182 to process the signal from the signal source 188. As such, the computer system 181 is a general purpose computer system that becomes a specific purpose computer system when executing the routine 187 of the present invention.

The computer system 181 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to exemplary embodiments, those skilled in the art will appreciate that various modifications and substitutions can be made thereto without departing from the spirit and scope of the invention as set forth in the appended claims.

What is claimed is:

1. A method for model based motion tracking of a catheter during an ablation procedure comprising:
receiving a training series of biplanar fluoroscopic images of a catheter, wherein each biplanar image is a pair of images in different planes acquired at a same time;
segmenting and processing the series of biplanar images to produce a distance transform image for each biplanar image at each acquisition time;
minimizing, for each pair of biplanar images at each acquisition time, a first cost function of the distance transform image for each pair of biplanar images to yield a translation parameter that provides a best fit for a 3-dimensional (3-D) model of the catheter to each pair of biplanar images at each acquisition time; and
calculating an updated catheter model for each acquisition time from said translation parameter,
wherein the first cost function is $$\sum_i (I_{DT,A,t}(P_{A,t} \cdot T_t^u(r_t) \cdot m_{i,t}) + I_{DT,B,t}(P_{B,t} \cdot T_t^u(r_j) \cdot m_{i,t})),$$

wherein $P_{A,t}$ and $P_{B,t}$ are projection matrices for biplanar image planes A and B, $I_{DT,At}$, $I_{DT,Bt}$ are the distance transform images for each image in the pair of biplane images at time t, $$T_t^u(r) = \begin{pmatrix} 1 & 0 & 0 & r_{t,x} \\ 0 & 1 & 0 & r_{t,y} \\ 0 & 0 & 1 & r_{t,z} \\ 0 & 0 & 0 & 1 \end{pmatrix}$$

is a transformation matrix for the fluoroscopic images at time t with translation parameters $r_t = (r_{t,x}, r_{t,y}, r_{t,z})^T$ and superscript u for 'unconstrained', respectively, and $m_{i,t}$ is the 3-D catheter model at time t, and the sum is over all points i in the catheter model,
wherein said catheter model is used to track a circumferential mapping catheter in a catheter ablation procedure using mono-plane fluoroscopic images acquired in real time.

2. The method of claim 1, wherein segmenting a biplanar image comprises using a cascade of weighted combinations of classification and regression trees (CARTs), wherein each CART is a weak classifier in which each node has a threshold associated with a feature that discriminates between a catheter and background and which partitions the feature space.

3. The method of claim 1, wherein processing the series of biplanar images comprises smoothing segmentation results with a median filter, thinning the smoothed segmentation, and calculating for every background pixel in each image a distance to a closest object pixel to produce the distance transform image.

4. The method of claim 1, wherein minimizing the first cost function comprises a multi-scale grid search that further comprises sub-sampling a search space and using a regions around a smallest cost function to initialize a search.

5. The method of claim 1, wherein the updated catheter model is calculated from $m_{i,t+1} = T_t^u(\hat{r}_t) \cdot m_{i,t}$ for all points i in the catheter model, wherein $\hat{r}_t$ represents a value of $r_t$ that minimizes the first cost function.

6. The method of claim 1, wherein the model center $\overline{m}_t$ for each updated catheter model is calculated from $$\overline{m}_t = \frac{1}{N} \sum_i m_{i,t},$$

where the sum is over all points i in the catheter model.

7. The method of claim 1, further comprising:
calculating a model center for each updated catheter model;
calculating a single motion vector from the model centers of the updated catheter models determining a viewing direction vector from a last row of a projection matrix from homogenous coordinates to a 3-D space;

determining a search direction vector perpendicular to the viewing direction vector and the single motion vector;

minimizing a second cost function of one distance transform image for each acquisition time, said cost function parameterized by said perpendicular search direction vector and said single motion vector to determine optimal coefficients of said perpendicular search direction vector and said single motion vector; and using said optimal coefficients with said perpendicular search direction vector and said single motion vector to update the catheter model at each acquisition time.

8. The method of claim 7, wherein calculating the single motion vector comprises performing a principal component analysis over all images.

9. The method of claim 7, wherein the second cost function is $$\sum_i I_{DT,t}(P \cdot T_c(\lambda, \mu) \cdot m_{i,t}),$$

wherein P is a projection matrix for one of the two biplanar images acquired for each time t, $I_{DT,t}$ is the distance transform image for the one biplanar image at each time t, wherein transformation matrix $$T_c(\lambda, \mu) = \begin{pmatrix} 1 & 0 & 0 & \lambda v_{p,x} + \mu v_{m,x} \\ 0 & 1 & 0 & \lambda v_{p,y} + \mu v_{m,y} \\ 0 & 0 & 1 & \lambda v_{p,z} + \mu v_{m,z} \\ 0 & 0 & 0 & 1 \end{pmatrix},$$

$\hat{\lambda}_t, \hat{\mu}_t$ are the optimal coefficients of the perpendicular search direction vector $v_p$ and the single motion vector $v_m$ with $v_p = (v_{p,x}, v_{p,y}, v_{p,z})^T$, $v_m = (v_{m,x}, v_{m,y}, v_{m,z})^T$, the index c is for 'constrained', and $m_{i,t}$ is the 3-D catheter model at time t, wherein the sum is over all points i in the catheter model.

10. A method for model based motion tracking of a catheter during an ablation procedure comprising:

receiving a training series of biplanar fluoroscopic images of a catheter, wherein each biplanar image is a pair of images in different planes acquired at a same time;

providing a series of 3-dimensional (3-D) catheter models updated from a single initial 3-D catheter model to correspond to each pair of biplanar images in said training series;

calculating a model center for each updated catheter model;

calculating a single motion vector from the model centers of the updated catheter models;

determining a viewing direction vector from a last row of a projection matrix from homogenous coordinates to a 3-D space;

determining a search direction vector perpendicular to the viewing direction vector and the single motion vector;

minimizing a first cost function of one distance transform image for each acquisition time, said cost function parameterized by said perpendicular search direction vector and said single motion vector to determine optimal coefficients of said perpendicular search direction vector and said single motion vector; and using said optimal coefficients with said perpendicular search direction vector and said single motion vector to update the catheter model at each acquisition time, wherein said catheter model is used to track a circumferential mapping catheter in a catheter ablation procedure using mono-plane fluoroscopic images acquired in real time.

11. The method of claim 10, wherein providing a series of catheter models comprises:

segmenting and processing the series of biplanar images to produce a distance transform image for each biplanar image at each acquisition time;

minimizing, for each pair of biplanar images at each acquisition time, the first cost function of the distance transform image for each pair of biplanar images to yield a translation parameter that provides a best fit of the single initial catheter model to each pair of biplanar images at each acquisition time; and calculating an updated catheter model for each acquisition time from said translation parameter.

12. A non-transitory program storage device readable by a computer, tangibly embodying a program of instructions executed by the computer to perform the method steps for model based motion tracking of a catheter during an ablation procedure, the method comprising:

receiving a training series of biplanar fluoroscopic images of a catheter, wherein each biplanar image is a pair of images in different planes acquired at a same time;

segmenting and processing the series of biplanar images to produce a distance transform image for each biplanar image at each acquisition time;

minimizing, for each pair of biplanar images at each acquisition time, a first cost function of the distance transform image for each pair of biplanar images to yield a translation parameter that provides a best fit for a 3-dimensional (3-D) model of the catheter to each pair of biplanar images at each acquisition time; and calculating an updated catheter model for each acquisition time from said translation parameter, wherein the first cost function is $$\sum_i (I_{DT,A,t}(P_{A,t} \cdot T_t^u(r_t) \cdot m_{i,t}) + I_{DT,B,t}(P_{B,t} \cdot T_t^u(r_j) \cdot m_{i,t})),$$

wherein $P_{A,t}$ and $P_{B,t}$ are projection matrices for biplanar image planes A and B, $I_{DT,At}, I_{DT,Bt}$ are the distance transform images for each image in the pair of biplane images at time t, $$T_t^u(r) = \begin{pmatrix} 1 & 0 & 0 & r_{t,x} \\ 0 & 1 & 0 & r_{t,y} \\ 0 & 0 & 1 & r_{t,z} \\ 0 & 0 & 0 & 1 \end{pmatrix}$$

is a transformation matrix for the fluoroscopic images at time t with translation parameters $r_t = (r_{t,x}, r_{t,y}, r_{t,z})^T$ and superscript u for 'unconstrained', respectively, and $m_{i,t}$ is the 3-D catheter model at time t, and the sum is over all points i in the catheter model, wherein said catheter model is used to track a circumferential mapping catheter in a catheter ablation procedure using mono-plane fluoroscopic images acquired in real time.

13. The computer readable program storage device of claim 12, wherein segmenting a biplanar image comprises using a cascade of weighted combinations of classification and regression trees (CARTs), wherein each CART is a weak classifier in which each node has a threshold associated with a feature that discriminates between a catheter and background and which partitions the feature space.

14. The computer readable program storage device of claim 12, wherein processing the series of biplanar images comprises smoothing segmentation results with a median filter, thinning the smoothed segmentation, and calculating for every background pixel in each image a distance to a closest object pixel to produce the distance transform image.

15. The computer readable program storage device of claim 12, wherein minimizing the first cost function comprises a multi-scale grid search that further comprises subsampling a search space and using a regions around a smallest cost function to initialize a search.

16. The computer readable program storage device of claim 12, wherein the updated catheter model is calculated from $m_{i,t+1} = T_t^u(\hat{r}_t) \cdot m_{i,t}$ for all points i in the catheter model, wherein $\hat{r}_t$ represents a value of $r_t$ that minimizes the first cost function.

17. The computer readable program storage device of claim 12, wherein the model center $\overline{\overline{m}}_t$ for each updated catheter model is calculated from $$\overline{m}_t = \frac{1}{N} \sum_i m_{i,t},$$

where the sum is over all points i in the catheter model.

18. The computer readable program storage device of claim 12, the method further comprising:
calculating a model center for each updated catheter model;
calculating a single motion vector from the model centers of the updated catheter models determining a viewing direction vector from a last row of a projection matrix from homogenous coordinates to a 3-D space;
determining a search direction vector perpendicular to the viewing direction vector and the single motion vector;
minimizing a second cost function of one distance transform image for each acquisition time, said cost function parameterized by said perpendicular search direction vector and said single motion vector to determine optimal coefficients of said perpendicular search direction vector and said single motion vector; and
using said optimal coefficients with said perpendicular search direction vector and said single motion vector to update the catheter model at each acquisition time.

19. The computer readable program storage device of claim 18, wherein calculating the single motion vector comprises performing a principal component analysis over all images.

20. The computer readable program storage device of claim 18, wherein the second cost function is $$\sum_i I_{DT,t}(P \cdot T_c(\lambda, \mu) \cdot m_{i,t}),$$

wherein P is a projection matrix for one of the two biplanar images acquired for each time t, $I_{DT,t}$ is the distance transform image for the one biplanar image at each time t, wherein transformation matrix $$T_c(\lambda, \mu) = \begin{pmatrix} 1 & 0 & 0 & \lambda v_{p,x} + \mu v_{m,x} \\ 0 & 1 & 0 & \lambda v_{p,y} + \mu v_{m,y} \\ 0 & 0 & 1 & \lambda v_{p,z} + \mu v_{m,z} \\ 0 & 0 & 0 & 1 \end{pmatrix},$$

$\hat{\lambda}_t, \hat{\mu}_t$ are the optimal coefficients of the perpendicular search direction vector $v_p$ and the single motion vector $v_m$ with $v_p = (v_{p,x}, v_{p,y}, v_{p,z})^T$, $v_m = (v_{m,x}, v_{m,y}, v_{m,z})^T$, the index c is for 'constrained', and $m_{i,t}$ is the 3-D catheter model at time t, wherein the sum is over all points i in the catheter model.

* * * * *